(12) United States Patent
Sonenberg et al.

(10) Patent No.: US 6,410,715 B1
(45) Date of Patent: Jun. 25, 2002

(54) METHODS FOR TREATING HORMONE DISORDERS

(75) Inventors: Nahum Sonenberg, Cote St. Luc (CA); Arnim Pause, Rockville, MD (US); Joe B. Harford, Redwood City; Vincent J. Miles, San Ramon, both of CA (US)

(73) Assignees: Questcor Pharmaceuticals, Inc., Union City, CA (US); Mc Gill University, Montreal (CA)

( * ) Notice: Subject to any disclaimer, the term of this patent is extended or adjusted under 35 U.S.C. 154(b) by 0 days.

(21) Appl. No.: 09/593,483

(22) Filed: Jun. 14, 2000

Related U.S. Application Data

(62) Division of application No. 09/256,331, filed on Feb. 23, 1999, now Pat. No. 6,111,077, which is a division of application No. 08/294,143, filed on Aug. 22, 1994, now Pat. No. 5,874,231.

(51) Int. Cl.[7] .............................................. C07H 21/04

(52) U.S. Cl. ...................................... 536/23.5; 536/23.1

(58) Field of Search ......................... 530/350; 536/23.5, 536/23.1; 514/44

(56) References Cited

U.S. PATENT DOCUMENTS

| | | | |
|---|---|---|---|
| 4,948,729 A | 8/1990 | Piatak et al. | 435/69.1 |
| 5,324,637 A | 6/1994 | Thompson et al. | 435/68.1 |
| 5,464,758 A | 11/1995 | Gossen et al. | 435/69.1 |
| 5,492,817 A | 2/1996 | Thompson et al. | 435/68.1 |

OTHER PUBLICATIONS

Yan et al (1992) J. Biol. Chem. 267:23226–23231.*
Morley et al (1991) J. Biol. Chem. 266: 4669–4672, Abstract only provided.*
Adams MD, Sequence identification of 2,375 human brain genes. Nature. Feb. 13, 1992;355(6361):632–4.
Avruch et al., 1985, "Protein Phosphorylation as a Mode of Insulin Action" in *Molecular Basis of Insulin Action*, Czech (ed.) Plenum Press, New York, pp. 263–296.
Belsham GJ and Brangwyn, A region of the 5' noncoding region of foot–and–mouth disease virus RNA directs efficient internal initiation of protein synthesis within cells: involvement with the role of L protease in translational control. J Virol. Nov. 1990;64(11):5389–95.
Belsham GJ, Reversibility of the insulin–stimulated phosphorylation of ATP citrate lyase and a cytoplasmic protein of subunit Mr 22000 in adipose tissue. Biochem J. Apr. 15, 1982;204(1):345–52.
Belsham GJ, Anti–insulin receptor antibodies mimic the effects of insulin on the activities of pyruvate dehydrogenase and acetylCoA carboxylase and on specific protein phosphorylation in rat epididymal fat cells. Diabetologia. Apr. 1980;18(4):307–12.

Blackshear PJ, Insulin and growth factors stimulate the phosphorylation of a Mr–22000 protein in 3T3–L1 adipocytes. Biochem J. Jul. 15, 1983;214(1):11–9.
Blanar MA and Rutter, Interaction cloning: identification of a helix–loop–helix zipper protein that interacts with c–Fos. Science. May 15, 1992;256(5059):1014–8.
Brannon PM, Adaptation of the exocrine pancreas to diet. Annu Rev Nutr. 1990;10:85–105.
Buse MG, Muscle protein synthesis: regulation of a translational inhibitor. Am J Physiol. Jun. 1984;246(6 Pt 1):E510–5.
Chien CT, The two–hybrid system: a method to identify and clone genes for proteins that interact with a protein of interest. Proc Natl Acad Sci U S A. Nov. 1, 1991;88(21):9578–82.
de Groot CJ, Developmental and hormonal regulation of carbamoyl–phosphate synthase gene expression in rat liver: evidence for control mechanisms at different levels in the perinatal period. Biochim Biophys Acta. Feb. 24, 1986;866(1):61–7.
De Benedetti A and Rhoads, Overexpression of eukaryotic protein synthesis initiation factor 4E in HeLa cells results in aberrant growth and morphology. Proc Natl Acad Sci U S A. Nov. 1990;87(21):8212–6.
Denton RM, A partial view of the mechanism of insulin action. Diabetologia. Oct. 1981;21(4):347–62.
Docherty K and Clark, Nutrient regulation of insulin gene expression. FASEB J. Jan. 1994;8(1):20–7.
Duncan R, Regulated phosphorylation and low abundance of HeLa cell initiation factor eIF–4F suggest a role in translational control. Heat shock effects on eIF–4F. J Biol Chem. Jan. 5, 1987;262(1):380–8.
Fagan RJ, Translational control of ornithine aminotransferase. Modulation by initiation factor eIF–4E. J Biol Chem. Sep. 5, 1991;266(25):16518–23.
Fields S and Song, A novel genetic system to detect protein–protein interactions. Nature. Jul. 20, 1989;340(6230):245–6.
Fuerst TR, Eukaryotic transient–expression system based on recombinant vaccinia virus that synthesizes bacteriophage T7 RNA polymerase. Proc Natl Acad Sci U S A. Nov. 1986;83(21):8122–6.
Gallie DR and Traugh, Serum and insulin regulate cap function in 3T3–L1 cells. J Biol Chem. Mar. 11, 1994; 269(10):7174–9.

(List continued on next page.)

*Primary Examiner*—Robert A. Schwartzman
*Assistant Examiner*—Bronwen M. Loeb
(74) *Attorney, Agent, or Firm*—Pennie & Edmonds LLP

(57) ABSTRACT

Method for screening for a non-hormone agent potentially useful to treat a hormone disorder The method involves contacting a potential agent with a system containing a cellular component and a translation factor. The component and factor interact with one another in an intact normal cell in a manner responsive to the hormone to cause a modulation of translation in the cell. The method involves determining whether the agent causes a modulation of translation by the component and the factor analogous to that which occurs in intact cells in response to the hormone.

2 Claims, 5 Drawing Sheets

OTHER PUBLICATIONS

Hager SR, Divergence between GLUT4 mRNA and protein abundance in skeletal muscle of insulin resistant rats. Biochem Biophys Res Commun. Nov. 27, 1991;181(1):240–5.

Hershey JW, Protein phosphorylation controls translation rates. J Biol Chem. Dec. 15, 1989;264(35):20823–6.

Hershey et al., 1996, *Translational Control*, Cold Spring Harbor Laboratory Press, pp. 245–269.

Hu C, Molecular cloning and tissue distribution of PHAS–I, an intracellular target for insulin and growth factors. Proc Natl Acad Sci U S A. Apr. 26, 1994;91(9):3730–4.

Joshi–Barve S, Alteration of the major phosphorylation site of eukaryotic protein synthesis initiation factor 4E prevents its association with the 48 S initiation complex. J Biol Chem. Feb. 15, 1990;265(5):2979–83.

Kaiser N, Differential regulation of glucose transport and transporters by glucose in vascular endothelial and smooth muscle cells. Diabetes. Jan. 1993;42(1):80–9.

Lazaris–Karatzas A and Sonenberg, The mRNA 5' cap–binding protein, eIF–4E, cooperates with v–myc or E1A in the transformation of primary rodent fibroblasts. Mol Cell Biol. Mar. 1992;12(3):1234–8.

Lazaris–Karatzas A and Sonenberg, Malignant transformation by a eukaryotic initiation factor subunit that binds to mRNA 5' cap. Nature. Jun. 7, 1990;345(6275):544–7.

Lazaris–Karatzas A, Ras mediates translation initiation factor 4E–induced malignant transformation. Genes Dev. Sep. 1992;6(9):1631–42.

Levenson RM, Insulin rapidly induces the biosynthesis of elongation factor 2. J Biol Chem. Jul. 15, 1989;264(20)11904–11.

Lin TA, PHAS–I as a link between mitogen–activated protein kinase and translation initiation. Science. Oct. 28, 1994;266(5185):653–6.

Lyons RT, Effects of fasting and insulin administration on polyribosome formation in rat epididymal fat cells. J Biol Chem. Jul 10, 1980;255(13):6330–4.

Manzella JM, Insulin induction of ornithine decarboxylase. Importance of mRNA secondary structure and phosphorylation of eucaryotic initiation factors eIF–4B and eIF–4E. J Biol Chem. Feb. 5, 1991;266(4):2383–9.

Merrick WC, Mechanism and regulation of eukaryotic protein synthesis. Microbiol Rev. Jun. 1992;56(2):291–315.

Methot N, The translation initiation factor eIF–4B contains an RNA–binding region that is distinct and independent from its ribonucleoprotein consensus sequence. Mol Cell Biol. Apr. 1994;14(4):2307–16.

Morgan HE, Regulation of protein synthesis in heart muscle. II. Effect of amino acid levels and insulin on ribosomal aggregation. J Biol Chem. Apr. 10, 1971;246(7):2163–70.

Morley SJ and Thomas, Intracellular messengers and the control of protein synthesis. Pharmacol Ther. 1991;50(3):291–319.

Morley SJ and Traugh, Differential stimulation of phosphorylation of initiation factors eIF–4F, eIF–4B, eIF–3, and ribosomal protein S6 by insulin and phorbol esters. J Biol Chem. Jun. 25, 1990;265(18):10611–6.

O'Brien C, Missing link in insulin's path to protein production. Science. Oct. 28, 1994;266(5185):542–3.

O'Leary NE, A translational inhibitor from muscles of diabetic rats: identification as histone H1. Am J Physiol. Jul. 1987;253(1 Pt 1):E81–9.

Ojamaa KM, Aminoacylation of initiator methionyl–tRNA(i) under conditions inhibitory to initiation of protein synthesis. Am J Physiol. Feb. 1993;264(2 Pt 1):E257–63.

Pause A, Insulin–dependent stimulation of protein synthesis by phosphorylation of a regulator of 5'–cap function. Nature. Oct. 27, 1994;371(6500):762–7.

Pelletier J and Sonenberg, Internal binding of eucaryotic ribosomes on poliovirus RNA: translation in HeLa cell extracts. J Virol. Jan. 1989;63(1):441–4.

Rhoads RE, Regulation of eukaryotic protein synthesis by initiation factors. J Biol Chem. Feb. 15, 1993;268(5):3017–20.

Rhoads RE, Mechanism of action and regulation of protein synthesis initiation factor 4E: effects on mRNA discrimination, cellular growth rate, and oncogenesis. Prog Nucleic Acid Res Mol Biol. 1993;46:183–219.

Serra D, Regulation of mitochondrial 3–hydroxy–3–methylglutaryl–coenzyme A synthase protein by starvation, fat feeding, and diabetes. Arch Biochem Biophys. Nov. 15, 1993;307(1):40–5.

Shantz LM and Pegg, Overproduction of ornithine decarboxylase caused by relief of translational repression is associated with neoplastic transformation. Cancer Res. May 1, 1994;54(9):2313–6.

Smith MR, Translation initiation factors induce DNA synthesis and transform NIH 3T3 cells. New Biol. Jul. 1990;2(7):648–54.

Smith CJ, Insulin–treated 3T3–L1 adipocytes and cell–free extracts derived from them incorporate 32P into ribosomal protein S6. Proc Natl Acad Sci U S A. May 1980;77(5):2641–5.

Sonenberg N, Reovirus mRNA can be covalently crosslinked via the 5' cap to proteins in initiation complexes. Proc Natl Acad Sci U S A. Oct. 1977;74(10):4288–92.

Stirewalt WS, The relation of RNA and protein synthesis to the sedimentation of muscle ribosomes: effect of diabetes and insulin. Proc Natl Acad Sci U S A. Jun. 1967;57(6):1885–92.

Vary TC, Role of elongation factor 2 in regulating peptide–chain elongation in the heart. Am J Physiol. Apr. 1994;266(4 Pt 1):E628–34.

Welsh GI and Proud, Evidence for a role for protein kinase C in the stimulation of protein synthesis by insulin in swiss 3T3 fibroblasts. FEBS Lett. Feb. 1, 1993;316(3):241–6.

Welsh GI, Glycogen synthase kinase–3 is rapidly inactivated in response to insulin and phosphorylates eukaryotic initiation factor eIF–2B. Biochem J. Sep. 15, 1993;294 ( Pt 3):625–9.

Welsh GI and Proud, Regulation of protein synthesis in Swiss 3T3 fibroblasts. Rapid activation of the guanine––nucleotide–exchange factor by insulin and growth factors. Biochem J. May 15, 1992;284 ( Pt 1):19–23.

* cited by examiner

1
ATG TCC GGG GGC AGC AGC TGC AGC CAG ACC CCA AGC CGG GCC ATC
met ser gly gly ser ser cys ser gln thr pro ser arg ala ile
                                                                15

46
CCC GCC ACT CGC CGG GTG GTG CTC GGC GAC GGC GTG CAG CTC CCG
pro ala thr arg arg val val leu gly asp gly val gln leu pro
                                                                30

91
CCC GGG GAC TAC AGC ACG ACC CCC GGC GGC ACG CTC TTC AGC ACC
pro gly asp tyr ser thr thr pro gly gly thr leu phe ser thr
                                                                45

136
ACC CCG GGA GGT ACC AGG ATC ATC TAT GAC CGG AAA TTC CTG ATG
thr pro gly gly thr arg ile ile tyr asp arg lys phe leu met
                                                                60

181
GAG TGT CGG AAC TCA CCT GTG ACC AAA ACA CCC CCA AGG GAT CTG
glu cys arg asn ser pro val thr lys thr pro pro arg asp leu
                                                                75

226
CCC ACC ATT CCG GGG GTC ACC AGC CCT TCC AGT GAT GAG CCC CCC
pro thr ile pro gly val thr ser pro ser ser asp glu pro pro
                                                                90

271
ATG GAA GCC AGC CAG AGC CAC CTG CGC AAT AGC CCA GAA GAT AAG
met glu ala ser gln ser his leu arg asn ser pro glu asp lys
                                                                105

316
CGG GCG GGC GGT GAA GAG TCA CAG TTT GAG ATG GAC ATT TAA
arg ala gly gly glu glu ser gln phe glu met asp ile (stop)
                                                                118

FIG.1

```
1
ATG TCC TCG TCA GCC GGC AGC GGC CAC CAG CCC AGC CAG AGC CGC
met ser ser ser ala gly ser gly his gln pro ser gln ser arg
                                                          15

46
GCC ATC CCC ACC CGC ACC GTG GCC ATC AGC GAC GCC GCG CAG CTA
ala ile pro thr arg thr val ala ile ser asp ala ala gln leu
                                                          30

91
CCT CAT GAC TAT TGC ACC ACG CCC GGG GGG ACG CTC TTC TCC ACC
pro his asp tyr cys thr thr pro gly gly thr leu phe ser thr
                                                          45

136
ACA CCG GGA GGA ACT CGA ATC ATT TAT GAC AGA AAG TTT CTG TTG
thr pro gly gly thr arg ile ile tyr asp arg lys phe leu leu
                                                          60

181
GAT CGT CGC AAT TCT CCC ATG GCT CAG ACC CCA CCC TGC CAT CTG
asp arg arg asn ser pro met ala gln thr pro pro cys his leu
                                                          75

226
CCC AAT ATC CCA GGA GTC ACT AGC CCT GGC ACC TTA ATT GAA GAC
pro asn ile pro gly val thr ser pro gly thr leu ile glu asp
                                                          90

271
TCC AAA GTA GAA GTA AAC AAT TTG AAC AAC TTG AAC AAT CAC GAC
ser lys val glu val asn asn leu asn asn leu asn asn his asp
                                                         105

316
AGG AAA CAT GCA GTT GGG GAT GAT GCT CAG TTC GAG ATG GAC ATC
arg lys his ala val gly asp asp ala gln phe glu met asp ile
                                                         120

361
TGA
 (stop)
```

FIG.2

```
  1                                                             50
  GTTCGCGGGT GCAGCGCACA GGAGATCATG TCCGGGGGCA GCAGCTGCAG

100
  CCAGACCCCA AGCCGGGCCA TCCCCGCCAC TCGCCGGGTG GTGCTCGGCG

150
  ACGGCGTGCA GCTCCCGCCC GGGGACTACA GCACGACCCC CGGCGGCACG

200
  CTCTTCAGCA CCACCCCGGG AGGTACCAGG ATCATCTATG ACCGGAAATT

250
  CCTGATGGAG TGTCGGAACT CACCTGTGAC CAAAACACCC CCAAGGGATC

300
  TGCCCACCAT TCCGGGGGTC ACCAGCCCTT CCAGTGATGA GCCCCCCATG

350
  GAAGCCAGCC AGAGCCACCT GCGCAATAGC CCAGAAGATA AGCGGGCGGG

400
  CGGTGAAGAG TCACAGTTTG AGATGGACAT TTAAAGCACC AGCCATCGTG

450
  TGGAGCACTA CCAAGGGGCC CCTCAGGGCC TTCCTGGGAG GAGTCCCACC

500
  AGCCAGGCCT TATGAAAGTG ATCATACTGG GCAGGCGTTG GCGTGGGGTC

550
  GGACACCCCA GCCCTTTCTC CCTCACTCAG GGCACCTGCC CCCTCCTCTT

600
  CGTGAACACC AGCAGATACC TCCTTGTGCC TCCACTGATG CAGGAGCTGC

650
  CACCAAGGGG AGTGACCCCT GCCAGCACAC CCTGCAGCCA AGGGCCAGGA

700
  AGTGGACAAG AACGAACCCT TCCTTCCGAA TGATCAGCAG TTCCAGCCCC

750
  TCGCTGCTGG GGGCGCAACC ACCCCTTCCT TAGGTTGATG TGCTTGGGAA

800
  AGCTCCCTCC CCCTCCTTCC CCAAGAGAGG AAATAAAAGC CACCTTCGCC

829
  CTAGGGCCAA GAAAAAAAAA AAAAAAAA
```

FIG.3

```
  1                                                          50
  CGGAAGCCCG CGCCCACAGC CATGTCCTCG TCAGCCGGCA GCGGCCACCA

250
  GCCCAGCCAG AGCCGCGCCA TCCCCACCCG CACCGTGGCC ATCAGCGACG

150
  CCGCGCAGCT ACCTCATGAC TATTGCACCA CGCCCGGGGG GACGCTCTTC

200
  TCCACCACAC CGGGAGGAAC TCGAATCATT TATGACAGAA AGTTTCTGTT

250
  GGATCGTCGC AATTCTCCCA TGGCTCAGAC CCCACCCTGC CATCTGCCCA

300
  ATATCCCAGG AGTCACTAGC CCTGGCACCT TAATTGAAGA CTCCAAAGTA

350
  GAAGTAAACA ATTTGAACAA CTTGAACAAT CACGACAGGA AACATGCAGT

400
  TGGGGATGAT GCTCAGTTCG AGATGGACAT CTGACTCTCC TGCAAGGATT

450
  AGAAGAAAAG CAGCAACACT GATACTTGTG TGCACCTGAT TTGGCCAATA

500
  GGATCAACAG TGAAAAGACA GAAGAGGCAA TACCAGCAGT CCCCATTACA

550
  GTCTCCACCT CCCCGTCTTC CTCTGGGTGC CAAATGATGG GAAGATGAGC

600
  TTCATCTGAC CATTTCTTCT CCCTGTCTCC TGTTCCCCTT CCCAGTTCCC

650
  AGTTAAACAG GTTAGATTGA AGGCCCTTGC TGTATTTCTG TAGAGCTAAG

700
  CAGCCCTTAG AGGAAAACAG TTCAACTCTG ACTTTCCTAG TTGTTTTTTT

750
  ATTGAGAGCC ACCCTCATAC CCTGTAATTT TGTCCCAAAT CAAATATCAA

800
  CCTACCAACA ACTGCCTGGC TGGGAAGTCT GGGGAAGGGA TACAGAGCTT

850
  GGTGGGCCTA ACACCATTCA TATTCCTTAC CCTCTGTCTC TCCTCCCTGT

900
  ATCCCACCTA TGGTTCAGTG TTGCAAGAGT CTGGGCTTGG GGTCTTTAAA
```

FIG.4A

```
                                                      950
ACCAGCAGGG GGAAATGATA AAAAGAGAGC TGCTTTCCCT TTTACCTTGA
                                                     1000
GGTATTCGTC CCTCGGGACA GAGCACAGCT TGTGCAACTC TGGTAGCGTT
                                                     1050
ACCCTTGTGC AACTCTGGTA GCGTTACCCT GTGACACTGT TTTGAGGTCC
                                                     1100
ACTTCCTTTC TTTCCTCTGG GAGGAATGTC TTCTGTCTTT GGTATTATAG
                                                     1150
TTCATCTTCC CATTCTTTTA CTTAGTGCAT TTGTGCAGAT ATTTTTAACT
                                                     1200
CTGTACATCA GAAGAGAGCC CTTGGTAACC AGTTTTGCTC TTCTTCTGCC
                                                     1250
ACTCCTCCCT GCTTGCATCT CGTTGCTGGC AGAGTCCTCT TGTACTTCAA
                                                     1300
GAAAGCAAAG TGATTTTGTC TGCCTCCTAG AGCAGGTCCA TACCAAGTAA
                                                     1350
TAGAGGCACT TTAGCTTCCA CTTGGTGGGT AAGGCCTGAT CATAGTATTC
                                                     1400
TGTCAGATAA TGCCTAAGAA TGACCGCTGG GGGTGGAGCT CCATCATCAA
                                                     1450
ATGGCCAATC TAGAACGTGG ATTCCTTCTT TTTCAACTGG AGCTTTATCA
                                                     1500
TATGTAGCAT CACAAACTCG AACCAAAGTC GTCACTCCAT ACTTCGGTAG
                                                     1550
CAGTCGACAG ATGAATTCCA GCTGAGCGCC GGTCGCTACC ATTACCAGTT
                                                     1600
GGTCTGGTGG GGGATCCACT AGTTCTAGAG CGGCCGCCAC CGCGTGGAGC
                                                     1650
TAATTCGCCC TATAGTGAGT CGTATTACAA TTCACTGGCC GTCGTTTTAC
             1673
AACGTCGTGA CTGGGAAACC TGG
```

FIG.4B

METHODS FOR TREATING HORMONE DISORDERS

The present application is a divisional application of application Ser. No. 09/256,331 filed on Feb. 23, 1999 (now U.S. Pat. No. 6,111,077) which is a divisional of application Ser. No. 08/294,143, filed Aug. 22, 1994 (now U.S. Pat. No. 5,874,231), both of which are hereby incorporated by reference in their entirety.

This invention relates to methods for screening for agents useful for treating hormone disorders, the novel agents identified using such screening methods, and their use to treat hormone disorders.

BACKGROUND TO THE INVENTION

Millions of people around the world suffer from conditions caused by hormone disorders, including diabetes, pituitary dwarfism and other hypopituitarisms, pituitary gigantism and other hyperpituitarisms, galactorrhea, hypothyroidism (myxedema) and hypothyroidism, a adrenocortical insufficiencies (e.g., Addison's disease) or hyperfunctions (e.g., Cushing's syndrome), pheochromocytoma, multiple endocrine neoplasias, polyglandular deficiency syndromes, and disorders of reproductive function.

Diabetes mellitus is a hormone disorder which afflicts millions of people annually. It is a serious and important health problem, involving 2 per cent or more of the US population. It is characterized by an inability to maintain homeostasis of glucose in the bloodstream. Thus the primary symptom of acute diabetes is hyperglycemia. A secondary set of symptoms arises in chronic or long-standing diabetes. These include degeneration of the walls of blood vessels, causing serious vascular complications involving both macro- and microvessels. Many different organs are affected by these complications, and common late clinical manifestations are retinopathy (chronic diabetes is a leading cause of blindness), nephropathy, neuropathy and foot ulcers.

In normal individuals, an increase in glucose concentration in the blood ("blood glucose") triggers the release of insulin from the pancreas into the bloodstream. This in turn leads to uptake of glucose into tissues and its conversion into glycogen and fatty acids. In most diabetic individuals there is a deficiency in the production, release, stability or uptake of insulin. This results in an inability to remove glucose from the bloodstream and to store its fuel content by metabolizing it into glycogen and fatty acids. Even in the presence of elevated blood glucose, the metabolism of a diabetic is geared towards the synthesis of glucose via gluconeogenesis and the oxidative breakdown of fatty acids.

Many other hormone disorders are characterized by an under- or over-abundance of the hormone in question, due to abnormalities in its synthesis, release or rate of elimination from the bloodstream, and/or by the inability of target cells to respond normally to the hormone, due to abnormalities in the number or function of receptors for the hormone or in the signal transduction pathways which mediate cells' responses to the hormone.

SUMMARY OF THE INVENTION

Applicant has determined that certain cellular components interact with translation factors in the cell and modulate cellular translation in response to a hormone. To this end, Applicant believes that agents which mimic this activity will be useful for treatment of hormone deficiencies. Applicant now provides a means to identify such useful agents. Thus, the present invention relates to methods for screening for agents useful to treat hormone disorders. The screening methods utilize a protocol in which potentially useful non-hormone agents are brought into contact with a system containing a cellular component and a translation factor which interact with one another in intact cells in a manner that is normally responsive to the hormone in question and results in a modulation of translation in the cell. The impact of the test agents on the interaction between the cellular component and the translation factor is then determined. Those agents which modify this interaction may be useful for the treatment of hormone disorders. Once identified, such agents can be formulated in therapeutic products (or even prophylactic products) in pharmaceutically acceptable formulations, and used for specific treatment of hormone disorders with few side effects. While such agents may be useful as hormone substitutes, they are also useful in test systems to allow an understanding of the action of the hormone.

Thus, in a first aspect, the invention features a method for screening for an agent useful to treat a hormone disorder by contacting a potential agent with a system containing a cellular component and a translation factor. The component and the factor have the property that they interact with one another in intact cells in a manner that is normally responsive to the hormone and results in a modulation of translation. The method also includes determining whether the agent causes a modification of any interaction between the component and the factor similar to any modification that would normally occur in intact cells in response to the hormone.

By "screening" is meant a process in which a large number of potentially useful agents are processed in the method of this invention. It is a process distinct from a single experiment in which a single agent is studied in detail to determine its method or mode of action.

By "high-throughput screening" is meant screening in which many potentially useful agents can be processed in a short period of time. By way of example, hundreds of the agents might be processed in a single day, or thousands in a single week.

By "hormone disorder" is meant any human or animal disease or condition caused by or characterized by abnormally high or low concentrations or availability of a hormone.

By "abnormally high" is meant any difference above normal sufficient to be manifested by physiological, biochemical, physical, mental, or psychological effects.

By "abnormally low" is meant any difference below normal sufficient to be manifested by physiological, biochemical, physical, mental, or psychological effects.

By "cellular component" is meant any component found within a cell. Such components include, but are not limited to, proteins, lipoproteins, glycoproteins, lipids, carbohydrates, nucleic acids, steroids, prostaglandins, and combinations and complexes thereof.

By "translation factor" is meant a molecule or group of molecules which participates directly at some stage in the process of translation but which is not permanently attached to or associated with the ribosome. Such factors include, but are not limited to, eIF-1, eIF-2 and its three known constituent polypeptides, eIF-2B (also known as GEF) and its five known constituent polypeptides, eIF-3 and its eight known constituent polypeptides, eIF-4A, eIF-4B, eIF-4C (also known as eIF-1A), eIF-4D (also known as eIF-5A), eIF-4E, eIF-4F and its three known constituent polypeptides, eIF-5, eIF-6 (also known as eIF-3A), eEF-1α, eEF-1βγ and its two known constituent polypeptides, eEF-2, and eRF.

By "interact with one another" is meant that the entities in question become physically associated with one another, transiently or for longer periods, or that one causes a biochemical or conformational change in the other.

By "normally responsive to the hormone" is meant that the molecule, molecules, complex or process in question undergoes some physical or biochemical alteration as a result of the presence, the absence, or a change in concentration of the hormone in question.

By "hormone" is meant any molecule or group of molecules released by a cell or cell type which has a physical or biochemical effect on the same or another cell or cell type. Such molecules include, but are not limited to, peptides and protein hormones such as insulin, glucagon, vasopressin, calcitonin, ACTH, growth hormone and the like, steroid hormones such as estrogen, testosterone and the like, and growth factors such as platelet-derived growth factor, epidermal growth factor, nerve growth factor, interleukins, other cytokines, and the like. Non-hormones are other components or other chemicals or biochemicals, as described below in "Libraries."

By "modulation of translation" is meant a control, or change of control, of the efficiency or rate of translation of mRNAs which results in a change in the overall rate of protein synthesis, the relative quantities of different proteins synthesized, and/or the quantities of individual proteins synthesized.

By "modification of any interaction between the component and the factor" is meant a change in the quantity of either participant involved in the interaction, in the relative quantities of the participants, in the affinity, stability or strength of their interaction, or in the rate constants for their association, dissociation, or alteration of one another.

A modification "similar to any modification that would normally occur in intact cells in response to the hormone" is a modification in which the change observed (as defined in the previous paragraph) involves the same participant or participants, and is of the same type and order of magnitude as the corresponding that normally occurs in intact cells in response to the hormone. Thus a parameter which normally increases in intact cells should increase in the system, and a parameter that normally decreases in intact cells should decrease in the system. Insofar as such a comparison can be performed, the extent of the increase or decrease in the system should preferably be at least 10%, preferably at least 25%, and most preferably at least 50% of the corresponding increase or decrease that normally occurs in intact cells in response to the hormone.

In preferred embodiments, the hormone disorder is diabetes mellitus and the hormone is insulin.

In further preferred embodiments, the cellular component which interacts with the translation factor is a protein which becomes phosphorylated in intact cells in response to the hormone.

By "phosphorylated" is meant that one or more phosphate groups is added to the protein, which may or may not already carry one or more phosphate moieties prior to the addition of the phosphate groups.

In further preferred embodiments, the modification in the interaction between the component and the factor is a reduction of the interaction. In more preferred embodiments, the reduction results in a stimulation of translation.

By "reduction of the interaction" is meant any reduction which can be detected in the absolute or relative quantity of either participant involved in the interaction, or in the affinity, stability or strength of their interaction, or in the rate constants for their association or their alteration of one another. Such a reduction is preferably at least two-fold, more preferably at least three-fold, and most preferably at least five-fold.

By "stimulation of translation" is meant any increase in the efficiency or rate of translation of mRNA which results in an increase in the overall rate of protein synthesis, in the relative quantities of different proteins synthesized, and/or in the quantities of an individual protein or proteins synthesized. Such an increase is preferably at least two-fold, more preferably at least three-fold, and most preferably at least five-fold.

In more preferred embodiments, the component is 4E-BP1, the factor is eIF-4E, and the system is an in vitro translation system in which the interaction between the 4E-BP1 and the eIF-4E is detected by translation of RNA sequences encoding one or more reporter polypeptides. More preferably, the RNA is capped and/or contains a 5'-untranslated region (5'-UTR) with significant secondary structure. More preferably, one of the reporter polypeptides in the enzyme luciferase.

By "4E-BP1" is meant the protein of 118 amino acids whose amino acid sequence is provided in FIG. 1, and which is encoded by the nucleic acid sequence therein. This protein has a molecular weight of about 12 kilodaltons (kD) but migrates anomalously during SDS/polyacrylamide gel electrophoresis, with an apparent molecular weight of approximately 22 kD. The protein binds to eIF-4E and causes inhibition of translation. Phosphorylation of this protein, for example in response to insulin, causes its release from eIF-4E and a consequent stimulation of translation.

By "eIF-4E" is meant the 25 kD protein also known as cap-binding protein which is a subunit of eIF-4F (also known as eIF-4), and whose function is to bind the cap at the 5'-end of mRNA molecules and assist in the association of these molecules with ribosomes at the initiation stage of translation.

By "in vitro translation system" is meant a cell-free extract capable of translating a protein or proteins from an RNA or RNAs encoding such proteins. Such a mixture typically contains ribosomes, tRNAs, amino acids, salts, and various other factors required to sustain protein synthesis, in addition to the RNA(s) that direct protein synthesis. Such mixtures are typically prepared from sources such as, but not limited to, rabbit reticulocytes, HeLa cells, wheat germ, and *E coli* cells; extracts prepared from such sources may be supplemented by the addition of tRNAs, amino acids, and so on, as necessary.

By "reporter polypeptide" is meant any protein which can be detected and measured by a physical, biochemical, enzymatic, immunological or other procedure.

By "5'-untranslated region with significant secondary structure" is meant a 5'-UTR which contains at least one sequence at least 30 nucleotides in length capable of forming by intrastrand base-pairing a second structure which impedes movement of a ribosome or ribosomal subunit along the RNA containing the 5'-UTR. The sequence should preferably begin within 50 nucleotides of the 5'-end of the RNA, and form a secondary structure with a free energy of at least −1 kcal/mol, preferably at least −2 kcal/mol, most preferably at least −5 kcal/mol for every ten nucleotides involved in the secondary structure.

By "luciferase" is meant any polypeptide, protein or part of a protein capable of catalyzing the conversion of luciferin to oxyluciferin with concomitant release of light. Examples of luciferases include, but are not limited to, the luciferase enzyme of the firefly *Photinus pyralis*, which has a molecular weight of approximately 65 kilodaltons.

In highly preferred embodiments, a modification to the interaction between the eIF-4E and the 4E-BP1 is detected by comparing translation of a first reporter polypeptide whose translation is dependent on eIF-4E with translation of a second reporter polypeptide whose translation is not dependent on eIF-4E. Preferably, the coding sequence for the second reporter polypeptide is translationally linked to an IRES. The coding sequences for the first and the second reporter polypeptides may be contained in separate RNAs, or in a bicistronic RNA, that is, an RNA containing coding sequences for two polypeptides. Said bicistronic RNA preferably contains an IRES between the coding sequences.

By "translation dependent on eIF-4E" is meant translation which requires eIF-4E for its initiation. Since a key role of eIF-4E is to bind to the cap structure found at the 5'-ends of eucaryotic mRNAs, translation of capped RNAs is dependent on eIF-4E. In in vitro translation systems mRNAs can usually be translated even if they are not capped. Such translation of uncapped mRNAs may nevertheless be dependent on eIF-4E, whose interaction with the other subunits of eIF-4 may be essential for the helicase activity of the eIF-4 which "melts secondary structure at and near the 5'-ends of mRNAs. In any specific case, it can be determined whether the translation of a particular mRNA is dependent on eIF-4E by determining whether this translation is reduced in the presence of additional 4E-BP1 or 4E-BP2.

By "4E-BP2" is meant the protein of 120 amino acids whose amino acid sequence is provided in FIG. 2, which is encoded by the nucleic acid sequence shown therein. This protein has a molecular weight of about 12 kilodaltons's (kD) but migrates anomalously during SDS/polyacrylamide gel electrophoresis, with an apparent molecular weight of approximately 20 kD. The protein binds to eIF-4E and causes inhibition of translation.

By "translation not dependent on eIF-4E" is meant translation which does not require eIF-4E for its initiation. A good example is translation which is initiated at an IRES. In any specific case, it can be determined whether translation of a particular mRNA is not dependent on eIF-4E by determining that this translation is not significantly reduced in the presence of additional 4E-BP1 or 4E-BP2.

A coding sequence which is "translationally linked" to an IRES is one which depends on the IRES for its translation. Typically, this means that the coding sequence is contained on same RNA molecule as the IRES and that the IRES is positioned adjacent to, and closer to the 5'-end than, the coding sequence.

By "IRES" is meant internal ribosome entry site, that is, a site within a RNA molecule which allows translation of that RNA to be initiated by the binding of a ribosome or subunit internally rather than at the cap structure the 5'-end. Such initiation can therefore take place independently of eIF-4E, and the activity of eIF-4E can be assessed by comparing translation of a protein which depends on cap-dependent initiation with translation of a protein which depends on IRES-mediated initiation. Preferably, the IRES is derived from the IRES region in the 5'-untranslated region (UTR) of a picornvirus RNA; the IRES is selected from the group consisting of enterovirus, rhinovirus, cardiovirus, aphthovirus, hepatitis A virus, hepatitis B virus and hepatitis C virus IRES sequences.

By "bicistronic RNA" is meant a RNA containing the coding sequences for two polypeptides. Preferably, translation of the first coding sequence, that is, the coding sequence closer to the 5'-end, is dependent on normal cellular initiation processes requiring eIF-4E, and translation of the other coding sequence is dependent on IRES-mediated initiation processes. Said bicistronic RNA may not need to be capped in order that the translation of the first coding sequence be eIF-4E-dependent. In the case of an uncapped bicistronic RNA, it can be determined whether the translation of the first coding sequence is dependent on eIF-4E by determining whether this translation is reduced in the presence of additional 4E-BP1 or 4E-BP2.

In further preferred embodiments, the determination of whether the agent causes a modification of an interaction between the component and the factor comprises measurement of binding of the component to the factor. In a more preferred embodiment, one of the component and the factor is attached to a solid phase and the other of the component and the factor is detected using an easily detectable reporter. Preferably, the component is 4E-BP1 and the factor is eIF-4E. Most preferably, the binding of the component to the factor is measured by measuring a protein translated in a cell from a RNA whose transcription depends on the binding.

By "binding" is meant a physical association between two or more molecules which is more prolonged and/or of greater strength or affinity than would be observed following random collisions of molecules that do not bind to one another. Such binding may be transient or for a longer period.

By easily detectable reporter is meant any agent or substance which can be readily detected by physical, chemical, biochemical, enzymatic or other means. Such reporters include, but are not limited to, enzymes, fluorescent, luminescent, or chromophoric molecules, antibodies labeled with any of the foregoing, and haptens and antigens that can be detected using such antibodies.

In a second aspect the invention provides a method for screening for an agent useful to treat a hormone disorder, comprising the steps of contacting a potential the agent with a system containing an enzyme which modifies a cellular component in a manner that is normally responsive to the hormone and results in a modulation of translation, and determining whether the agent causes an increase or decrease in the activity of the enzyme.

By "an enzyme which modifies a cellular component" is meant an enzyme which catalyzes a chemical change of that component. Such chemical changes may include, but are not limited to, the addition or removal of phosphate groups, carbohydrate moieties, lipid moieties, nucleotidyl moieties, and the like; and oxidations, reductions, dehydrogenation, hydrogenations, and the like.

In preferred embodiments, the enzyme which modifies the cellular component is a kinase.

By "kinase" is meant an enzyme which adds a phosphate group or phosphate groups to the component, which may or may not already contain phosphate moieties prior to the addition of the phosphate group or groups.

In preferred embodiments, the enzyme which modifies the cellular component is a phosphatase.

By "phosphatase" is meant an enzyme which removes a phosphate group or phosphate groups from the component, which may or may not retain other phosphate moieties following the removal of the phosphate group or groups.

In additional preferred embodiments, the hormone is insulin and the component is 4E-BP1.

In a third aspect, the invention features a method of treating a patient with a hormone disorder by administering, in a therapeutically effective dose, a pharmaceutically acceptable formulation of an agent which causes a modification of an interaction between a cellular component and a translation factor, where the component and the factor have the property that they interact with one another in intact cells in a manner that is normally responsive to the hormone and results in a modulation of translation.

By "therapeutically effective dose" is meant an amount that relieves (to some extent) one or more symptoms of the disease or condition in the patient. Additionally, by "therapeutically effective dose" is meant an amount that returns to normal, either partially or completely, physiological or biochemical parameters associated with or causative of a hormone disorder. Generally, it is an amount between about 1 nmole and 1 μmole of the molecule, dependent on its $EC_{50}$ and on the age, size, and disease associated with the patient.

By "pharmaceutically acceptable formulation" is meant a pharmaceutical composition prepared for storage and subsequent administration, which comprise a pharmaceutically effective amount of an agent as described herein in a pharmaceutically acceptable carrier or diluent. Acceptable carriers or diluents for therapeutic use are well known in the pharmaceutical art, and are described, for example, in *Remington's Pharmaceutical Sciences*, Mack Publishing Go. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id The invention features agents formulated for use in treatment of hormone disorders, and any such unique (i.e., previously unknown) formulations are within this invention.

In preferred embodiments, the invention features methods of treating a patient with diabetes by administering an agent effective to reduce the interaction between the component and the factor. In more preferred embodiments, the component is 4E-BP1 and the factor is eIF-4E.

In a seventh aspect, the invention features a purified cellular component that binds to eIF-4E and causes a modulation of translation in a cell in response to a hormone.

In preferred embodiments, the component comprises the protein 4E-BP1 or the protein 4E-BP2.

In an eighth aspect, the invention provides a purified nucleic acid sequence encoding a cellular component that binds to eIF-4E and causes a modulation of translation.

By purified is meant that the protein or nucleic acid is separated from the environment in which it naturally occurs, and is preferably in a homogeneous form suitable for use in test assays as described herein. Such components are useful in the assays described below.

In preferred embodiments, the sequence codes for the protein 4E-BP1 or for the protein 4E-BP2.

Other features and advantages of the invention will be apparent from the following description of the preferred embodiments thereof, and from the claims.

BRIEF DESCRIPTION OF THE DRAWINGS

FIG. 1 depicts the base sequence of the sense strand of the open reading frame in a CDNA clone which encodes human eIF-4E-binding protein 4E-BP1, and the predicted amino acid sequence of this protein (SEQ. ID NO. 1).

FIG. 2 depicts the base sequence of the sense strand of the open reading frame in a CDNA clone which encodes human eIF-4E-binding protein 4E-BP2, and the predicted amino acid sequence of this protein (SEQ. ID NO. 2).

FIG. 3 depicts the DNA sequence of a cDNA encoding 4E-BP1; 829 bases of the sense strand are shown (SEQ. ID NO. 3). The ATG start codon and TM stop codon which delineate the open reading frame for 4E-BP1 are underlined.

FIGS. 4A–4B depicts the DNA sequence of a cDNA encoding 4E-BP2; 1673 bases of the sense strand are shown (SEQ. ID NO. 4). The ATG start codon and TGA stop codon which delineate the open reading frame for 4E-BP2 are underlined.

DESCRIPTION OF THE PREFERRED EMBODIMENTS

The present invention provides novel methods for identifying agents useful for the treatment of hormone disorders, and for using novel agents so identified to treat such disorders. The methods of this invention are based on the observation that cellular components can interact with translation factors in a manner that is responsive to hormones and modulates translation.

Hormones are important substances in multicellular organisms, and in particular animals and humans, which help coordinate the overall response of an organism to its environment.

Translation is the cellular process by which proteins are synthesized in accordance with instructions encoded within the genetic information of the cell. Because proteins such as enzymes, receptors, and the like have an enormous influence on the cell, translation plays a central role in the metabolism of the cell. Reflecting this, when a cell responds to an external signal such as a hormone, translation generally responds too, and the translational response is an important part of the response of the cell to the hormone.

In hormone disorders there is typically a deficiency or an excess of a particular hormone, or an altered ability of target cells to respond to the hormone. As a result, the target cells do not exhibit the normal translational responses triggered by the hormone, such as changes in the overall rate of protein synthesis and in the relative quantities of individual proteins synthesized. The inability of the cells to exhibit the normal translational responses is an important factor contributing to the physical, physiological and clinical manifestations of the hormone disorder.

The present invention relates to methods for procuring normal translational responses to a hormone in cells which are not receiving or responding to the hormone. The inventors have identified cellular components which interact with a translation factor in a manner which modulates translation and is normally responsive to a hormone; the components are thus involved in mediating the action of the hormone. The invention features methods for identifying agents which modify the interaction between cellular components and translation factors in a manner similar to that which normally occurs in response to a hormone. Agents identified by the methods are preferably small organic molecules which are absorbed when ingested orally. Such agents are then formulated in pharmaceutically acceptable compositions and administered in therapeutically effective doses to individuals suffering from hormone disorders.

Such agents have significant advantages over existing agents for the treatment of hormone disorders, such as insulin and sulfonylurea drugs used for the treatment of diabetes.

Treatment of diabetes caused by insulin deficiency is often accomplished by administration of insulin, requiring frequent and regular subcutaneous injections. Administration by this route is inconvenient and painful. Moreover, great care must be exercised not to administer too much insulin, which can cause severe hypoglycemia, even leading to loss of consciousness and death. Even when insulin is administered carefully, the blood glucose of a diabetic individual often fluctuates both above and below the normal range for a non-diabetic individual. These fluctuations are believed to be responsible for the long-term health problems (such as blindness) experienced even by patients who are treated with insulin injections.

Certain diabetic individuals may be treated with oral hypoglycemic drugs rather than insulin. These are individuals with so-called non-insulin dependent (Type II) diabetes mellitus; the drugs in question are sulfonylurea drugs such as glyburide, chlorpropamide, glipizide and tolbutamide which stimulate release of insulin from the pancreas. Patients may become unresponsive or poorly responsive to such drugs over time, and there is still a risk of excessive hypoglycemia with such drugs. Sulfonylurea-induced hypoglycemia can be severe and may last or recur for days after treatment is stopped. There is a significant mortality rate in patients with sulfonylurea-induced hypoglycemia, and it has been recommended that all such patients be hospitalized. Moreover, chronic administration of oral hypoglycemic drugs has been reported to be associated with a significantly increased cardiovascular mortality (*Diabetes* 19, supp. 2,747–830, 1970).

There is thus a need for improved drugs for treating diabetes mellitus which are more convenient to administer than insulin, avoid the side-effects of oral hypoglycemic drugs, and carry a reduced risk of inducing severe hypoglycemia. It is an object of the present invention to provide methods for discovering such improved drugs.

Many other hormone disorders require administration of hormones to supplement natural deficiencies, or drugs to simulate or counteract the biological effects of hormones that are missing or overabundant. In many cases, hormones or drugs must be injected and/or have significant side-effects. For some disorders there are no satisfactory therapies available; not unusually, surgical intervention is required. There is thus a need for improved drugs for the treatment of many hormone disorders.

Translation

Translation is the final stage of the pathway by which cells use genetic information to make proteins. For a gene to be expressed, that is, for the product it encodes to be synthesized, the gene is transcribed to provide a messenger RNA (mRNA) molecule, which then directs synthesis of the protein encoded by the gene in the process known as translation. This process involves the polymerization of amino acids in a sequence specified by the nucleotide sequence of the mRNA; successive groups of three nucleotides in the RNA known as codons, each specify which amino acid should be added next in the polymerization process.

Translation occurs on a structure known as the ribosome, composed of ribosomal RNA and ribosomal proteins. Successive amino acids are brought to the ribosome by transfer RNAs (tRNAs). Each ribosome consists of two subunits, known as the large (60S) subunit and the small (40S) subunit. Translation of a particular mRNA begins with the stage known as initiation. A tRNA carrying the first amino acid required (which is almost invariably methionine) attaches to the small ribosomal subunit to form a 43S complex. Next, the mRNA attaches to this complex to form a 48S complex, with three bases of the methionyl-tRNA base-paired with the AUG start codon in the mRNA. (The three bases of a tRNA which base-pair with a codon in the mRNA are known as the anticodon). Then, the large ribosomal subunit joins the 48S complex to complete the initiation complex.

The process then moves into the elongation stage, which involves successive cycles with the following steps. The process begins with the growing peptide chain attached to a tRNA occupying a site in the ribosome known as the P-site. (in the first cycle of elongation, there is only one amino acid, methionine, in the chain). A new aminoacyl-tRNA then arrives at an adjacent site on the ribosome known as the A-site. Which aminoacyl-tRNA becomes attached at the A-site is determined by base-pairing between the mRNA currently aligned with this site and the anticodon of the tRNA component of the incoming aminoacyl-tRNA; a "proof-reading" check is performed to ensure that the correct aminoacyl-tRNA is occupying the A-site. Next, the peptide chain on the tRNA occupying the P-site is transferred, and joined, to the amino acid on the (aminoacyl-) tRNA occupying the A-site. The whole ribosome then moves or "translocates" along the mRNA by a distance corresponding to one codon. As a result, the tRNA carrying the growing peptide chain, which was formerly occupying the A-site, is now in the P-site, and the A-site is now vacant to accept the next incoming aminoacyl-tRNA. The tRNA which formerly carried the growing peptide chain is now in a site known as the exit site and is subsequently lost.

Multiple cycles of elongation continue until the ribosome eventually comes to a termination codon (also known as a stop codon) in the mRNA. There are three such codons, UUA, UUG, and UGA. A ribosome reaching such a codon stops translation, whereupon the ribosome and the protein molecule it has just synthesized are leased from the mRNA. The ribosome dissociates into its two subunits, which may subsequently go through the whole process again by participating in the formation of new initiation complexes.

Many factors, known as translation factors, are required in addition to the ribosome and aminoacyl-tRNAs in order for translation to occur. Translation factors typically participate in translation at one particular step rather than throughout the whole process as the ribosome does. They are grouped into classes on the basis of the step in translation at which they act. Thus there are initiation factors, elongation factors, and termination or release factors. Within each class, these factors are grouped into further classes according to their specific function, within a particular step of translation. Thus eukaryotic initiation factors (eIFs) are divided into factors of the eIF-1 class, involved with pleiotropic stimulation of initiation complex assembly; the eIF-2 class, involved in binding the initiator methionyl-tRNA to the 40S subunit to form the 43S complex; the eIF-3 class, involved in preparation of the 40S subunit; the eIF-4 class, involved in binding of mRNA to the 43S complex to form the 48S complex; and the eIF-5 class, involved in releasing an eIF-2 factor from the 48S complex and in the joining of the 60S subunit. Eukaryotic elongation factors (eEFs) include the eEF-1 class, involved in binding of aminoacyl-tRNAs to the ribosome, and eEF-2, involved in translocation of the ribosome. In eukaryotes there is only one known termination or release factor, eRF (in prokaryotes three such factors are known).

The regulation of translation has been studied in a variety of ways. In one sense, translation is a typical metabolic process which must be regulated to balance the available energy resources, the growth requirements of the cell, and the signals being received by the cell from its environment, such as those communicated by hormones. Unlike other cellular processes, however, the products of translation (such as enzymes, receptors, and so on) directly affect many other cellular processes. It might therefore be expected that the rate of translation would be controlled by a larger number of input signals and a more diverse array of control mechanisms than other biochemical pathways. In practice, however, whereas the number of input signals has turned out to be large, as expected, the array of control mechanisms appears to be relatively small (Rhoads, *J. Biol. Chem.* 268, 3017–3020, 1993). Thus protein synthesis is regulated in most cases by changes in the cellular concentration" or Phosphorylation state of just a few translation factors.

The two most important such factors established to date for regulating translation are eIF-2 and eIF-4E (Rhoads, Ibid.). Various physiological events lead to an increase in phosphorylation of the α-subunit of eIF-2. Two enzymes have been characterized in animal cells which phosphorylate eIF-2α, known respectively as protein kinase, RNA-activated (PKR, also known as p68, DAI and various other names) and heme-controlled repressor (HCR). Both these kinases are activated under conditions which are unfavorable for the cell and in which continuing protein synthesis would make the situation worse: viral infections, heme deprivation, heat shock, and the like. Phosphorylation of eIF-2α causes it to bind tightly to a recycling factor, eIF-2B (also known as GEF); this effectively locks eIF-2 in an inactive state, and prevents it from participating in further initiation events, which in turn effects a pronounced reduction in the rate of translation.

The role of eIF-4E in translation has been the subject of various investigations (reviewed in Rhoads, ibid, and in Rhoads et al. *Progr. Nucl. Acids Res. Mol. Biol.* 46, 183–219, 1993). eIF-4E is a 25 kD protein that specifically binds the cap structure found at the 5'-end of cellular mRNAs (Sonenberg & Shatkin, *Proc. Natl. Acad. Sci. USA* 74, 4288–4292, 1977), and is involved in binding of mRNA to the small ribosomal subunit during formation of the preinitiation complex. It is associated with other proteins [eIF-4A, p220 (eIF-4γ)], in the complex known as eIF-4F (also known as eIF-4). Some preparations of eIF-4F also contain a fourth protein, eIF-4B. eIF-4E appears to be the rate-limiting factor for translation in cells, and a major point of regulation of protein synthesis. Such regulation may be achieved at least in part by phosphorylation of eIF-4E; phosphorylation is required for activity, and there are multiple phosphorylation sites on the protein. A variety of physiological events have been reported to lead to coordinated changes in eIF-4E phosphorylation and protein synthesis (summarized in Rhoads, 1993): mitosis, heat shock, adenovirus infection; treatment with phorbol 12-myristate 13-acetate, lipopolysaccharide, tumor necrosis factor-α, insulin, serum, epidermal growth factor, platelet-derived growth factor, nerve growth factor, or interleukin-1; and expression of pp60$^{src}$ or p21$^{ras}$.

The role of eIF-4E in regulating translation is underscored by the observation that overexpression of eIF-4E in various cultured lines of immortalized cells causes those cells to acquire a transformed phenotype (de Bendedetti Rhoads, *Proc. Natl. Acad. Sci. USA* 87, 8212, 1990, Lazaris-karatzas & Sonenberg *Nature* 345, 644, 1990. Similarly, micro injection of eIF-4E also causes initiation of mitosis and morphological transformation (Smith et al. *New Biol* 2, 648, 1990). Lazaris-Karatzas et al. (*Genes & Devl* 6, 1631–1642, 1992) showed that overexpression of eIF-4E caused activation of the ras oncogene and that the transformed phenotype can be reversed by overexpression of GAP, the negative effector of ras. Lazaris-Karatzas & Sonenberg (*Mol. Cell. Biol* 12, 1234–1238, 1992) reported that eIF-4E can only transform primary rat embryo fibroblasts if special selective conditions are used for cell culture, but that eIF-4E will cooperate with other known oncoproteins, v-myc or E1A, to transform these cells. Overexpression of eIF-4E may cause transformation by facilitating translation of mRNAs involved in cellular growth which are otherwise translated relatively poorly because they contain long 5'-UTRs with significant secondary structure (Rhoads et al., 1993; Rhoads, 1993). Selective enhancement of translation in cells overexpressing eIF-4E has been reported for ornithine aminotransferase (Fagan et al. *J. Biol. Chem.* 266, 16518–16523, 1991) and for a luciferase cistron placed downstream of the 5'-UTR of ornithine decarboxylase (Shantz & Pegg, *Cancer Res.*, 54, 2313–2316, 1994).

Other examples of phosphorylation of translation factors have been reported (reviewed in Hershey, *J. Biol. Chem.* 264, 20823–20826, 1989, and Merrick, *Microbiol. Rev.* 56, 291–315, 1992). Thus phosphorylation has also been reported for eIF-2B, eIF-3, eIF-4B, eIF-4γ, eIF-5, eEF-1α, eEF-1β, eEF-1γ, eEF-1δ, and EF-2. Although it is conceivable that regulation of translation by phosphorylation of numerous polypeptides could occur, the most compelling evidence, as detailed above, supports regulation by phosphorylation of only two: eIF-4E and eIF-2α.

Insulin

There have been various reports that insulin has an impact on protein synthesis and induces phosphorylation of intracellular proteins.

An early report on the effects of insulin on protein synthesis was provided by Stirewalt et al. (*Proc. Natl. Acad. Sci. USA* 57, 1885–1892, 1967), who found that insulin treatment leads to a rapid recruitment of ribosomes to form polysomes, and that this does not require the synthesis of new mRNA. The observations of Morgan et a. (*J. Biol. Chem.* 246, 2163–2170, 1970) indicated that insulin accelerates steps involved in initiation of peptide chains. Lyons et at. (*J. Biol. Chem.* 255, 6330–6334, 1980). drew a similar conclusion based on their determination that insulin causes an increase in the number of initiated ribosomes, in their synthetic activity in vitro, and in the apparent protein synthetic activity of the cell. Smith et al. (*Proc. Natl. Acad. Sci. USA* 77, 2641–2645, 1980) reported that ribosomal protein S6 is phosphorylated in response to insulin. Morley & Traugh (*J. Biol. Chem.* 265, 10611–10616, 1990) extended this observation by reporting that several other proteins involved in translation are phosphorylated in response to insulin, namely eIF-4F, eIF-4B, eIF-3; within eIF-4F it is the p25 (eIF-4E) and p220 subunits which are phosphorylated. Duncan et al. (*Proc. Natl. Acad. Sci. USA* 262, 380–388, 1987) had previously reported that initiation factor eIF-4F is a multiprotein cap-binding complex containing three major proteins, p220, eIF-4A, and p28 (also known as cap-binding protein I and eIF-4E), and that phosphorylation of p28 (eIF-4E) may play a role in regulating the initiation of translation. Joshi-Barve et al. (*J. Biol. Chem.* 265, 2979–2983, 1990) reported that phosphorylation increases the activity of eIF-4E. Manzella et al.(J. Biol. Chem. 266, 2383–2389, 1991) reported, like Morley & Traugh, that insulin stimulates phosphorylation of initiation factors eIF-4B and eIF-4E. Welsh & Proud (*Biochem. J.* 284, 19–23, 1992) reported that insulin rapidly activates eIF-2B. Welsh & Proud (*Biochem. J.* 294, 625–629, 1993) provided evidence that glycogen synthase kinase-3 phosphorylates eIF-2B and is rapidly inactivated in response to insulin. Gallie and Traugh (*J. Biol. Chem.* 269, 7174–7179, 1994) reported that insulin stimulates the translation of capped but not of uncapped mRNAs, and suggested that insulin enhanced the function of the cap-binding complex.

As well as causing an overall stimulation of protein synthesis, insulin stimulates the biosynthesis of about 25 proteins over and above its general effect on protein synthesis (Levenson et al. *J. Biol. Chem.* 264, 11904–11911, 1989). About 75% of these stimulations did not require active transcription, suggesting that insulin preferentially stimulates translation of pre-existing mRNAs for the proteins in question. Manzella et al. (*J. Biol. Chem.* 266, 2383–2389, 1991) suggested a mechanism for such preferential stimulation, namely the phosphorylation of initiation factors (specifically eIF-4B and eIF-4E) involved in melting secondary structures in the 5'-untranslated regions (5'-UTRs) of mRNAs, providing a preferential stimulation of the translation of certain mRNAs whose 5'-UTRs contain extensive secondary structure, such as the mRNA encoding ornithine decarboxylase.

Various other proteins not known to be involved in translation have been reported to be phosphorylated in response to insulin. These include ATP citrate lyase, acetyl CoA carboxylase, triacylglycerol lipase, and the alpha subunit of pyruvate dehydrogenase (Belsham et al, *Diabetologia*, 21, 347–362, 1981; Avruch et al. in "Molecular Basis of insulin Action, Czech, M.P., ed., pp 67–94, Plenum Press, New York, 1985). Several research groups have described one particular protein with an apparent molecular weight of 22 kilodaltons (kD) which becomes phosphorylated in response to insulin. Thus Belsham et al. (*Diabetologia*, 18, 307–312, 1980; *Biochem. J.* 204, 345–352, 1982) describe this as one of three proteins phosphorylated in rat adipose tissue in response to insulin, and speculate that it is the protein inhibitor $I_1$ which inhibits the general phosphoprotein phosphatase. Blackshear et al. (*Biochem. J.* 214, 11–19, 1983) also describe a similar protein from mice rather than rats which has a molecular weight of 22 kD and becomes phosphorylated in response to insulin, to epidermal growth factor and to platelet-derived growth factor. Avruch et at (ibid.) also refer to a protein with a molecular weight of 22 kD but state that it is not protein phosphatase inhibitor 1 or 2 (as speculated by Belsham et al.), and that "to date there is no evidence on the identity of this . . . protein". Finally, Hu et al. (*Proc. Natl. Acad. Sci. USA* 91, 3730–3734, 1994) describe the molecular cloning and tissue distribution of a rat protein "PHAS-I" which is phosphorylated in response to insulin, and is the same as the protein with an apparent molecular weight of 22 kD previously described by other authors. The true molecular weight of this protein is in fact 12.4 kD, but the protein migrates anomalously during SDS/polyacrylamide gel electrophoresis, with an apparent molecular weight of 21 kD. Like previous authors, Hu et al. were unable to ascribe a function to this protein.

The sequence of a partial human cDNA designated HFBCE72 was determined by Adams et al. (*Nature* 355, 632–634, 1992) as part of a project to determine the sequences of randomly selected clones from a cDNA library. This sequence was placed in the GenBank database with an accession number M78575, and applicant notes appears to correspond to part of the sequence of 4E-BP1. The authors made no other investigation into the protein encoded by this sequence and ascribe no function to this protein.

In contrast to the positive effects of insulin on translation, the diabetic state reportedly leads to an impairment of translation, attributed to defects in both initiation (Ojaama et al., *Am. J. Physiol.* 264, E257–E263, 1993) and elongation (Vary et al., *Am. J. Physiol.* 264, E628–E634, 1994). Buse et al. (*Am. J. Physiol.* 246, E510–E515, 1984) described a heat- and acid-stable protein which appears to inhibit translational initiation in rabbit reticulocyte lysate, and whose inhibitory activity increases upon induction of diabetes. The same research group later reported that this inhibitory protein has a molecular weight of 30–32 kD and is in fact histone H1 (O'Leary et al., *Am. J. Physiol.* 253, E81–E89, 1987).

Hormone Disorders

Various hormone disorders are already known in the art, and methods established by which additional such disorders can be identified. Typically, a disorder is identified by establishing a correlation between a particular set of symptoms and an abnormality in the amount of hormone circulating in the bloodstream and/or in the physiological and/or biochemical response of the target tissue or cells to the hormone.

Hormones which trigger translational responses can be readily identified by a variety of means. So, for example, cells or tissues can be treated with a hormone in the presence of radioactive amino acids, and the nature and quantity of radioactive proteins synthesized can be compared with those observed in cells and tissues which have not been treated with the hormone. Methods such as electrophoresis, isoelectric focusing, and the like can be used as appropriate to separate the proteins for this comparison. Proteins from treated and untreated cells and tissues can also be compared without radioactive labeling, using staining, immunochemical, or various other procedures known in the art. Rather than radioactive amino acids, cells or tissues can also be provided with other radiochemicals which will enable specific covalent modifications of cellular components and/or translation factors which occur in response to a hormone to be detected. Radioactive phosphate, for example, can be used to detect proteins which become phosphorylated in response to the hormone, radioactive sugars to detect components which become glycosylated, and so on.

Translation Factors

Translation factors are identified by a variety of means known to those skilled in the art, such as those used to identify currently known factors as listed above. So, for example, cellular extracts are prepared and tested for their ability to synthesize proteins from endogenous or exogenously added mRNA or to stimulate protein synthesis in in vitro translation systems. Protein synthesis is followed by monitoring the incorporation of labeled amino acids, for example, radiolabeled amino acids, into acid-precipitable material. The extracts are then fractionated by a variety of procedures known to those skilled in the art and fractions identified that, individually or in combination, are essential for and/or stimulate the translation of proteins in vitro. After repeated rounds of fractionation through various fractionation procedures, with tests performed at each round to identify fractions active in or required for translation, relatively pure preparations are obtained which contain putative translation factors. Confirmation that a substance purified in this manner is a translation factor is obtained using procedures such as "addback" experiments, in which protein synthesis is compared in an in vitro translation system depleted of the putative translation factor and in the system to which the putative factor has been added back. The precise role played by a putative factor is explored and identified using assays known in the art which are designed to focus on a particular stage of the translation process, such as the formation of preinitiation complexes or initiation complexes, or the elongation or termination stages of translation. Such assays feature, for example, the use of sucrose density gradients to study "polysome profiles" or the formation of complexes, of highly purified preparations of ribosomes, ribosomal subunits, aminoacyl-tRNAs, and/or other known translation factors, of radiolabeled preparations of the putative factor or other participants in the translation process, of chemical cross-linking procedures and labeling procedures to identify participants which are close to one another during translation, of radio labeling techniques such as pulse-chase experiments, of kinetic and binding studies to identify rate constants, association and dissociation constants, of enzymatic assays to measure consumption or production of substances such as ATP and GTP, and so on. Various other means are also used to identify translation factors and their role in translation. Immunochemical or immunocytochemical techniques are used,for example, to determine that a protein against which an antibody has been prepared is associated with ribosomes or other translation factors.

Procedures such as gel-retardation assays can be used to identify proteins that bind to RNA and are then found to play a role in translation. A search can be conducted for interactions between known translation factors and previously unknown factors, for example by cross-linking studies, by the identification or isolation of complexes involving the known translation factors and previously unknown factors, by detection in cell extracts of proteins that bind to known translation factors, and by the use of systems such as the two-hybrid system (Fields & Song, *Nature*, 340, 245–246, 1989; Chien et al., *Proc. Natl. Acad. Sci. USA* 88, 9578–9582, 1991), in which interactions between two proteins in vivo are required to reconstitute a transcription factor necessary for the expression of a reporter protein. Molecular cloning experiments enable homologies to be identified between the DNA and/or protein sequences of a protein and those for known translation factors or RNA-binding proteins or RNA helicases or other proteins known to be involved in translation. Genetic experiments are used to identify genes whose function is required for or has an impact on translation. Genetic studies in yeast, for example, of that organism's response to amino acid starvation have led to the identification of a number of genes for proteins that participate in and/or regulate translation.

From the above descriptions it will be evident that there are a number of approaches which one skilled in the art can adopt in order to identify translation factors.

Cellular Components

Cellular components for use in the methods of this invention are identified by various means. Several general approaches can be adopted. In one, components are first identified that interact with translation factors; the components are then investigated further to determine whether their interactions with the translation factors undergo changes in response to a hormone and modulate translation. In a second general approach, components are first identified that undergo changes in response to a hormone; the components are then investigated further to determine whether they interact with translation factors, and whether the changes observed in response to the hormone modify the interactions between the components and the factors in a manner that modulates translation. In a third general approach, cellular components are identified by comparing cells or tissues which exhibit the behavior associated with the hormone disorder with cells or tissues that do not, and identifying components specifically associated with the disorder.

The first step in the first of the general approaches is the identification of components that interact with translation factors. Such components are identified in various ways. In the examples cited herein, the components 4E-BP1 and 4E-BP2 were identified by using labeled translation factor eIF-4E as a probe to find clones in a cDNA library that were expressing proteins capable of interacting with the eIF4E. A similar approach can be adopted to identify any cellular component interacting with a translation factor. Labeled translation factors can also be used to probe "Western blots" made by transferring proteins to a sheet of a suitable support from an electrophoresis gel in which they have previously been separated, or thin-layer chromatograms on which cellular components had been separated, or samples spotted onto a solid support of fractions collected from density gradients, chromatograms, or from any other form of separation performed on a cell extract.

In alternative approaches, one or more translation factors is used to capture or purify such components from cell extracts. In one such approach, the factors are mixed with an extract prepared from cells, or with samples prepared by fractionation of such an extract, and an analysis performed to determine whether the translation factor(s) have interacted with any components in the extract. The analysis is performed, for example, by immunoprecipitation with an antibody specific for the translation factor(s), followed by electrophoresis or centrifugation on sucrose density gradients under non-denaturing and denaturing conditions to determine the molecular weights of any complexes in which the factor(s) had become involved and of cellular components participating in the complexes. Similar analyses can be performed using binding proteins such as streptavidin or avidin instead of or in addition to an antibody in order to capture complexes involving the translation factor(s); in this case the factor should first be labeled with a ligand recognized by the binding proteins, such as biotin. In another approach, a translation factor is used as a ligand on a chromatography matrix to purify by affinity chromatography cellular components that interact with the factor. In a further approach, cross-linking studies are performed to identify cellular components and translation factors which interact with" one another.

Cellular components that are proteins which interact with translation factors that are proteins can also be identified by any procedures suitable for detecting and analyzing protein:protein interactions. They can, for example, be identified using the two-hybrid system (Fields & Song, *Nature*, 340, 245–246, 1989; Chien et al., *Proc. Natl. Acad. Sci. USA* 88, 9578–9582, 1991), in which interactions between two proteins in vivo are required to reconstitute a transcription factor necessary for the expression of a reporter protein. This system requires the availability of a gene or cDNA encoding one of the two proteins which interact with each other. For the purposes of this invention, this gene or cDNA encodes a translation factor, and is cloned into a specific plasmid in such a way that it is expressed fused to the DNA-binding domain of a yeast transcriptional activator such as GAL4 which has two separable and functionally essential domains, one for DNA-binding and the other for transcriptional activation. In parallel, genes or cDNAs encoding cellular components that may bind to the translation factor are cloned in such a way that each such component is expressed fused to the transcriptional activation domain of the same DNA-binding protein. Introduction of both types of fusion into the same yeast cell results in generation of functional DNA-binding protein only if the fusion partners of the two domains of this protein interact with one another closely enough to bring together its two separately-expressed domains. Clones which produce such functional DNA-binding protein are selected very easily by plating them on a medium which requires the yeast to produce an enzyme that is under the control of the DNA-binding protein. The gene or cDNA for the cellular component which binds to the translation factor is then recovered from yeast clones which grow on the selective medium.

Cellular components which interact with translation factors can also be identified by adding cellular extracts, or fractions thereof, to biochemical assays or in vivo assays which measure the activities of individual translation factor, of translation factors in groups, or of the complete translational apparatus. Such assays were described above in connection with the identification of translation factors, and can be used to monitor the fractionation and purification of a cellular component found to interact with a translation factor or factors. If some effect is observed in such an assay in response to addition of a cellular component identified in this way, the specific of the component for a particular translation factor is illustrated by adding an excess of various such factors to the assay; in many cases an excess of the factor with which the component interacts will reverse the effect of the component.

As well as helping to identify cellular components that interact with translation factors, biochemical and in vivo assays as just described also provide information about the manner in which any interaction observed modulates translation. These assays can also be used to obtain such information for cellular components which are initially identified in an assay, such as a binding assay, that does not directly provide such information. So, for example, biochemical assays can be performed which determine whether the interaction stimulates or inhibits translation, whether its effect is specific for certain mRNAs or general, and so on.

Many of the approaches described above are illustrated in the examples cited herein, in which the interaction of 4E-BP1 and 4E-BP2 with eIF-4E was demonstrated in several ways, First, by the method used initially to identify the 4E-BP1 and 4E-BP2, as described above. Second, by demonstrating that a labeled eIF-4E derivative could bind to recombinant fusion proteins containing 4E-BP1 and 4E-BP2 respectively which had been separated by electrophoresis and blotted onto a nitrocellulose membrane. Third, by demonstrating that immunoprecipitates obtained using an antibody directed against 4E-BP1 also contained eIF-4E. Fourth, by demonstrating that in the presence of eIF-4E, but not in its absence, 4E-BP1 binds to an affinity purification matrix whose ligand consists of cap, structures to which eIF-4E binds. Fifth, by demonstrating using a bicistronic RNA in an in vitro translation system that cap-dependent translation, which is mediated by eIF-4E, is inhibited by the addition of recombinant fusion proteins containing 4E-BP1 or 4E-BP2, whereas cap-independent translation mediated by an IRES element is not; and that the inhibition of cap-dependent translation can be relieved by addition of excess eIF-4E. And sixth, by demonstrating that cap-dependent translation from bicistronic RNAs in vitro is reduced in cells transfected with plasmids encoding 4E-BP1 or 4E-BP2, whereas IRES-dependent translation from the bicistronic RNAs is not.

One skilled in the art will readily recognize how similar approaches and techniques can be applied to identify and characterize the interactions between other cellular components and translation factors.

Once a cellular component has been identified that interacts with a translation factor, various approaches are used to determine whether the interaction between the component and the factor is responsive to a hormone. Cells or tissues normally responsive to the hormone are treated with the hormone, and the status of the component, the factor and their interaction compared with the status of each in untreated cells. Various methods are used to study the component, the factor, and the interaction. So, for example, any of the methods described above for identifying the interaction between the component and the factor is used to determine whether the interaction is changed in hormone-treated cells or extracts therefrom compared with untreated cells or extracts therefrom.

Additional methods can also be employed to identify changes which occur in response to treatment with a hormone. So, for example, the treatment of cells or tissues with the hormone is conducted in the presence of radioactive precursors of the component or the factor, which are then both examined for changes in quantity, in charge properties (as evidenced by, for example, mobilities in electrophoresis or isoelectric focusing procedures, and behavior in ion-exchange chromatography), in conformation (as evidenced by behavior in sedimentation analyses, and by measurements of circular dichroism, nuclear magnetic resonance, and the like), or in any other parameter that relates to the interaction between the component and the factor and the impact of the interaction on translation. If a particular covalent modification of either the component or the factor is considered possible or likely in response to treatment with the hormone, specific tests for the covalent modification are performed. So, for example, phosphorylation or dephosphorylation of the component and/or the factor is detected by providing cells or tissue with radioactive phosphate during treatment with the hormone, and comparing the incorporation of the phosphate into the component and the factor with that observed in cells or tissue not treated with the hormone. Similarly, glycosylation of the component and the factor is studied by providing cells with an appropriate radioactive sugar, and other covalent modifications by providing other appropriate radioactive precursors.

The methods just described for identifying changes in cellular components which occur in response to hormones are readily adapted to measure the activity of enzymes responsible for the changes. So, for example, if such methods reveal that a cellular component of interest becomes phosphorylated in response to a hormone, an assay is developed in which the activity of the enzyme or enzymes responsible for the phosphorylation is measured by following incorporation of radioactive phosphate into the component. Conversely, if it is found that a cellular component of interest becomes dephosphorylated in response to a hormone, an assay is developed in which the activity of the enzyme or enzymes responsible for the dephosphorylation is measured by following loss of radioactive phosphate from the component. Similarly, other assays can be readily developed for the enzymes responsible for other changes observed in cellular components in response to hormones.

Such assays can be used to purify the enzymes, by monitoring the distribution of the enzymes during fractionation procedures applied to cell extracts. Once purified, an enzyme of interest is used to raise antibodies and to determine a partial or complete protein sequence, providing tools that are then used to identify in a gene or cDNA library clones that contain a gene or cDNA encoding the enzyme, Alternatively, a cDNA expression library is screened by dividing its members into pools of clones and assaying for the activity of the enzyme in extracts from the pools. In consecutive rounds of screening, positive pools are separated into several smaller pools and the assays repeated, until individual clones expressing the enzyme are identified.

In the case where a cDNA or gene is available which encodes a cellular component that interacts with a translation factor, it is also useful to search libraries of known DNA and protein sequences for homologous DNA and protein sequences, and if homologous proteins are found to determine whether anything is known concerning the response of these proteins to hormone treatment.

In the examples cited herein, such an approach led to the identification of the human protein 4E-BP1 as being homologous to PHAS-I, a rodent protein known to become phosphorylated in cells treated with insulin. It was then established that treatment of cells with insulin led to a marked reduction (about 3–4 fold) in the amount of 4E-BP1 which can interact with eIF-4E, even though the total amount of 4E-BP1 remained the same; that treatment of extracts from such cells with potato acid phosphatase restored the ability of 4E-BP1 to interact with eIF-4E to a level similar to that seen in extracts from untreated cells; that the amount of 4E-BP1 which binds to a "cap-column" [which uses $m^7G(5')ppp(5')G$, also known as $m^7GDP$, as an affinity ligand] via binding to eIF-4E which has bound to the $m^7GDP$ is reduced in extracts from treated cells compared with extracts from untreated cells; and that when cells were incubated with inorganic [$^{32}P$]-phosphate, the amount of eIF-4E that could be immuno-precipitated with antiserum against 4E-BP1 (PHAS-I) was reduced in extracts from insulin-treated cells, but that phosphorylation of 4E-BP1 was increased in such cells. Taken together, these data clearly demonstrate that insulin causes an increase in phosphorylation of 4E-BP1 and a reduction in its interaction with eIF-4E.

The second general approach to identifying cellular components useful in the methods of this invention is to start by identifying components that undergo changes in response to a hormone, and then investigate these components further to determine whether they interact with translation factors in a manner that is responsive to the hormone and modulates translation. Many of the procedures just described for the first general approach to identifying such components— beginning with a translation factor and then identifying hormone-responsive components that interact with it—are also useful for the second approach, and are simply applied in a different sequence. So, for example, the first step can be a side-by-side comparison of extracts prepared from cells or tissues provided with a radiolabeled precursor (such as a phosphate or a sugar) and either treated or not treated with a hormone. Such extracts are then fractionated and analyzed by any known procedure, such as electrophoresis, isoelectric focusing, chromatography, differential centrifugation or the like, and components identified which change in response to treatment with the hormone. Interactions of such components with translation factors, and the effects of such interactions upon translation, are then identified by any of the procedures described above.

In a third general approach, cellular components are identified by comparing cells or tissues which exhibit the behavior associated with the hormone disorder with cells or tissues that do not, and identifying components specifically associated with the disorder. So, for example, adipose tissue from a diabetic animal is compared with similar tissue from a non-diabetic animal, and cellular components identified which in the diabetic animal are more or less abundant than, more or less phosphorylated than, more or less glycosylated than, or differ in any other identifiable respect from, the corresponding components in the non-diabetic animal. These components are then studied further to determine whether they interact with translation factors in a manner that is responsive to the hormone and modulates translation.

Drug Assays

Cellular components and translation factors identified as described above can be utilized in a variety of methods of this invention to discover drugs useful for treating hormone disorders. The methods feature systems in which potential drugs can be tested to determine whether they cause a modification of the interaction between a cellular component and a translation factor similar to that which would normally occur in intact cells in response to the hormone. The systems of this invention are configured such that the interaction and/or the modification of the interaction can be readily detected, and if appropriate, measured.

Such a configuration is achieved in a variety of ways. One attractive general approach is to use a translation system in which the synthesis of an easily detectable reporter polypeptide is dependent upon or influenced by the interaction. Such a system comprises, for example, an in vitro translation system in which a RNA is translated which encodes the firefly luciferase enzyme, whose synthesis can easily be detected by measuring luciferase activity. To establish reference points for the interpretation of test results, the RNA is translated in extracts prepared from hormone-treated cells ("treated extracts") and in similar extracts from untreated cells ("untreated extracts"). Untreated extracts are then used in high-throughput screening to identify agents which modulate translation of the RNA in these extracts so that it is similar to the translation of the RNA observed in treated extracts. To enhance the selectivity of the assay, the untreated extracts used for the screening may be supplemented with purified or semi-purified preparations of the cellular component and/or the translation factor from untreated cells.

This approach is also enhanced by designing the in vitro translation system to reflect specific properties or functions of the cellular component and translation factor of interest. The translation factor eIF-4E and the cellular component 4E-BP1 of this invention can be used to illustrate this approach. The 4E-BP1 binds to eIF-4E in a manner that inhibits translation; insulin treatment leads to phosphorylation of the 4E-BP1 and its release from eIF-4E, stimulating translation. Agents which cause a modification of the interaction between 4E-BP1 and eIF-4E similar (i.e., analagous in result, even if not in level of interaction modification) to that caused by insulin can be identified in an in vitro translation system which is highly dependent on the function of eIF-4E. A suitable such system is an in vitro translation system which utilizes capped mRNAs. Such RNAs require functional eIF-4E in order to be translated. This reflects the function of eIF-4E, which is to bind the cap structure found at the 5'-end of cellular RNAs as an essential step in the initiation of translation. An agent which stimulates translation of a reporter polypeptide, such as luciferase, from a capped RNA may be doing so by causing a modification in the interaction between eIF-4E and 4E-BP1 similar to that which occurs in response to insulin. To assess the specificity of the agent for the eIF-4E/4E-BP1 interaction, the effect of the agent on translation which does not depend upon eIF-4E for initiation is determined. One method for this determination is to examine the effect of the agent on IRES-dependent translation of a reporter polypeptide, that is, on translation of the polypeptide from coding sequences positioned downstream of an IRES in the RNA being translated. An IRES or "internal ribosome entry site" is a site which allows translation of a RNA to be initiated by the binding of a ribosome internally rather than at the cap structure at the 5'-end. Such IRES elements are found in the 5-untranslated regions (UTRs) of the RNAs of picornvirus such as enterovirus, rhinovirus, cardiovirus, aphthovirus, and hepatitis A virus, and in some other viral RNAs as well.

The specificity of the agent for the eIF-4E/4E-BP1 interaction can also be assessed by examining the effect of supplementing the in vitro translation mixture with additional 4E-BP1 and/or eIF-4E. So, for example, if an agent interacts specifically with 4E-BP1 in a manner that reduces the interaction of the 4E-BP1 with eIF4E, the presence of additional 4E-BP1 is expected to increase the amount of an agent required to exert the same effect on cap-dependent translation as is observed in the absence of the additional 4E-BP1. Or, for example, if an agent interacts specifically with eIF-4E or with the interface between eIF-4E and 4E-BP1 in a manner that reduces the interaction of the eIF-4E with 4E-BP1, the presence of additional eIF-4E is expected to increase the amount of an agent required to exert the same effect on cap-dependent translation as is observed in the absence of the additional eIF-4E.

The use of a capped RNA with a 5'-UTR containing significant secondary structure also enhances the specificity of translation assays relating to 4E-BP1 and eIF-4E, because such RNAs are highly dependent upon eIF-4F (of which eIF-4E is a crucial component) for translation. The use of such RNAs may therefore accentuate any effects observed on eIF-4E-dependent translation. 5'-UTRs that contain significant secondary structure include, but are not limited to, the 5'-UTRs of ornithine decarboxylase and various protooncogenes and growth factors. A 5'-UTR with significant secondary structure is also readily generated by inserting a palindromic sequence into the DNA encoding the 5'-UTR of any mRNA. This is readily achieved by inserting multiple copies of a restriction enzyme "linker" into a site within the 5'-UTR, as described in Example 12 herein.

To compare cap-dependent and IRES-mediated translation, a single bicistronic RNA can be used to direct translation. Such a RNA contains coding sequences (cistrons) for two polypeptides, with a cellular UTR upstream of the first cistron and an IRES downstream of it, between the first cistron and the second cistron. The first cistron closer to the 5'-end of the mRNA is translated via cap-dependent initiation; the second cistron is translated via IRES-dependent initiation. An agent that modifies the eIF-4E/4E-BP1 interaction causes a boost in the synthesis of protein from the first cistron significantly greater than any boost observed in synthesis from the second cistron.

Bicistronic RNAs for such assays are prepared by in vitro transcription of appropriate DNA templates constructed by methods well known in the art. For example, the methods of recombinant DNA technology are used to construct a template with the following sequences in the following order a promoter for a phage RNA polymerase, such as SP6, T7 or T3 RNA polymerase; a sequence encoding the 5'-UTR of a cellular mRNA, such as β-globin mRNA or a mRNA whose 5'-UTR includes significant secondary structure, such as ornithine decarboxylase; a sequence encoding a first reporter polypeptide, with a stop codon encoded at the 3'-end of such sequence; a sequence encoding an IRES element, such as an IRES from rhinovirus, encephalomyocarditis virus (EMCV) or some other picornvirus; a sequence encoding a second reporter polypeptide; and a recognition sequence for a restriction enzyme whose recognition sequence is not found in any of the preceding sequences just listed. To prepare bicistronic RNA for use in a translation assay for modifiers of the eIF-4Et4E-BP1 interaction, the template is linearized by cleavage of the recognition sequence for the restriction enzyme, and transcribed using the phage RNA polymerase in the presence of a "cap analog", such as the dinucleotide $m^7G(5')ppp(5')G$, in addition to the four ribonucleoside triphosphates (NTPs). This generates capped bicistronic RNA for use in in vitro translation reactions in cell extracts.

Comparison of cap-dependent and IRES-dependent translation can also be performed with the cap-dependent and the IRES-dependent translation directed by separate RNAs rather than a single bicistronic RNA. Thus two separate RNAs are used, one a capped RNA encoding a first reporter polypeptide, and the second an IRES-containing RNA encoding the same or a second reporter polypeptide. Preferably, the second RNA is still a bicistronic RNA, even though translation of the "upstream" cistron closer to the 5'-end may not be monitored; the presence of the upstream cistron and its stop codon ensures that any translation observed of the "downstream" cistron is indeed dependent upon IRES-mediated initiation.

Extracts for the translation of RNAs are prepared by a variety of methods known to those skilled in the art, from sources such as rabbit reticulocytes, wheat germ, HeLa cells, and the like. The extract may usefully be treated with micrococcal nuclease to destroy endogenous cellular mRNAs, so that RNA added to the extract is essentially the only RNA translated. Appropriate nuclease-treated extracts are available from a variety of commercial sources, such as Promega of Madison, Wis., Novagen of Madison, Wis., Life Technologies of Gaithersburg, Md., and several others.

Preparations of cellular components such as 4E-BP1 and of translation factors such as eIF-4E which are to be added to in vitro translation extracts to test the specificity of agents for the interaction between a cellular component and a translation factor are prepared by various methods known in the art, such as by purification from cells containing normal amounts of the components and factors or from cells containing cloned genes expressing relatively large quantities of the components and factors, either in their native forms or as moieties within fusion proteins that are readily purified by virtue of some property of the fusion partners in such proteins.

Cap-dependent and IRES-dependent translation can also be studied in intact cells rather than cell extracts. Thus cells are transfected by procedures well known in the art with DNA constructs similar to those described above for in vitro transcription of bicistronic RNAs, if necessary with the phage RNA polymerase promoter replaced by, or supplemented by, a promoter active in the cells being transfected. Agents are then tested to determine their impact on synthesis of reporter polypeptides translated via cap-dependent and IRES-dependent translation. An agent which stimulates cap-dependent translation significantly more than IRES-dependent translation is potentially an agent which modifies the interaction between eIF-4E and 4E-BP1 in a manner similar to that which occurs in response to insulin and which modulates translation. Further information about the specificity of the agent is obtained by assessing its impact on translation in cells that express elevated levels of eIF-4E and/or 4E-BP1 as a result of being transfected with DNA constructs coding for the eIF4E and/or 4E-BP1.

Proteins suitable for use as reporters in the methods of this invention include, but are not limited to, easily assayed enzymes such as β-galactosidase, luciferase, β-glucuronidase, chloramphenicol acetyl transferase, and secreted embryonic alkaline phosphatase; proteins for which immunoassays are readily available such as hormones and cytokines; proteins which confer a selective growth advantage on cells such as adenosine deaminase, aminoglycoside phosphotransferase (the product of the neo gene), dihydrofolate reductase, hygromnycin-B-phosphotransferase, thymidine kinase (when used with HAT medium), xanthine-guanine phosphoribosyltransferase (XGPRT), and proteins which provide a biosynthetic capability missing from an auxotroph; proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin or diphtheria toxin.

It will be evident to those skilled in the art that the principles underlying the procedures just described above in connection with eIF-4E and 4E-BP1 can be readily applied to other cellular components and translation factors to establish methods by which agents can be tested to determine their impact on interactions between the components and factors.

Another general approach to utilizing the methods of this invention involves procedures in which the binding between a cellular component and a translation factor is examined. Binding interactions between two or more "binding partners" are measured in a variety of ways. One approach is to label one of the partners with an easily detectable label, place it together with the other partner in conditions under which they would normally interact, perform a separation step which separates bound labeled partner from unbound labeled partner, and then measure the amount of labeled partner bound. The effect of a test agent included in the binding reaction is determined by comparing the amount of labeled partner which binds in the presence of this agent to the amount which binds in its absence.

The separation step in this type of procedure can be accomplished in various ways. In one approach, the unlabeled partner is immobilized on a solid phase prior to the binding reaction with the labeled partner, and unbound labeled partner is removed after the binding reaction by washing the solid phase. Attachment of the binding partner to the solid phase is accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step is accomplished after the labeled partner has been allowed to interact with the unlabeled partner in solution. If the size difference between the labeled partner and the unlabeled partner permits such a separation, the separation is achieved by passing the products of the binding reaction through an ultrafilter whose pores allow passage of unbound labeled partner but not of labeled partner bound to unlabeled partner. Alternatively, the products of the binding reaction are passed through a gel filtration matrix which separates labeled partner which has bound to unlabeled partner from unbound labeled partner. This can be achieved very conveniently by choosing a gel filtration matrix whose exclusion limit is greater than the molecular size of labeled partner by itself and less than the molecular size of the complex formed by labeled partner bound to unlabeled partner; the complex passes through the gel filtration set-up in the void volume, while unbound labeled partner is eluted significantly later.

In another type of approach, separation is achieved using any reagent capable of capturing the unlabeled partner from solution, such as an antibody against the unlabeled partner, a ligand-binding protein which can interact with a ligand previously attached to this partner, and so on.

If the cellular component that binds to the translation factor of interest is a protein, its interaction with the factor can be monitored in the two-hybrid system described above. Thus a yeast strain is constructed in which a transcription factor that controls the synthesis of a detectable reporter can only be provided by the interaction between the component and the factor, because the interaction is required to bring together two separate functional domains of the transcription factor, each of which domains is expressed in the yeast strain as a fusion protein fused to one or other of the component and the factor. Agents which may potentially modify the interaction between the component and the factor are tested to determine their impact of production in the strain of the reporter.

In further general methods of this invention, agents are tested to determine whether they increase or decrease the activity of an enzyme which modifies a cellular component in a manner that is normally responsive to a hormone and results in a modulation of translation. Methods for identifying such enzymes and measuring their activities were described above. The effect of a test agent on the activity of such an enzyme is measured using cell extracts which contain the enzyme, or using enzyme purified from cells in which the enzyme is normally expressed, or using enzyme purified from cells in which the enzyme is expressed at elevated levels from a cloned gene or cDNA. Similarly, the cellular component which is the substrate for the enzyme is provided in the form of a cell extract containing the component (which may be the same cell extract that provides the enzyme) or as a purified preparation from cells in which the component is normally expressed, or from cells in which the component is expressed at elevated levels from a cloned gene or cDNA.

Many of the experimental procedures which are useful in implementing the methods of this invention are collected in reference texts such as Ausubel F et al. (eds) *Current Protocols in Molecular Biology*, Wiley-Interscience, New York, 1991, and Sambrook et al., *Molecular Cloning: A Laboratory Manual* (2nd Ed.), Cold Spring Harbor Laboratory Press, Cold Spring Harbor, N.Y., 1989.

Libraries

The methods encompassed by this invention can be used to screen agent libraries to discover novel drugs for treating hormone disorders. Such libraries may comprise either collections of pure agents or collections of agent mixtures. Examples of pure agents include, but are not necessarily limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active principle from the mixture for characterization and development as a therapeutic drug. In particular, the mixture so identified can be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

In preferred embodiments, the methods of this invention are used for high-throughput drug discovery assays in conjunction with the above mentioned libraries. The assays are performed in any format that allows rapid preparation and processing of multiple reactions such as in, for example, multi-well plates of the 96-well variety. In more preferred embodiments, stock solutions of the test agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay. Examples of such detectors include, but are not limited to, luminometers, spectrophotomers, colorimeters, and fluorimeters, and devices that measure the decay of radioisotopes.

In another embodiment, the methods are used to screen combinatorial libraries of random peptides, oligonucleotides or other chemical entities produced by any of the techniques already in the public domain or otherwise. known to those skilled in the art. Because of their large size, these libraries are likely sources of lead agents since they can contain from $10^7$–$10^{10}$ chemical entities.

Once an agent has been determined using the methods of this invention to cause an appropriate modification of the interaction between a cellular component and a translation factor which interact with one another in a manner that is normally responsive to a hormone and modulates translation, the agent can be tested for its utility in treating hormone disorders which involve the hormone. Such testing is performed initially in tissue-culture models and animal models of the disorder, and subsequently in human subjects. The adsorption, distribution, metabolism and excretion of the agent is characterized, and its potential toxicity is assessed in acute, sub-chronic and chronic studies.

Administration

For administration to subjects, agents for treating hormone disorders are formulated in pharmaceutically acceptable compositions. The compositions can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonically, rectally, vaginally, nasally, orally, transdermally, topically, ocularly, intraperitoneally, or as suitably formulated surgical implants employing a variety of dosage forms. As will be readily apparent to one skilled in the art, the useful in vivo dosage to be administered and the particular mode of administration will vary depending upon the mammalian species treated, the particular composition employed, and the specific use for which these compositions are employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved.

The dosage for the compositions of the present invention can range broadly depending upon the desired affects and the therapeutic indication. Typically, dosages will be between about 0.01 μg and 100 mg/kg, preferably between about 0.01 and 10 mg/kg, body weight. Administration is preferably per os on a daily or as-needed basis.

Orally-administered formulations can be prepared in conventional forms, including capsules, chewable tablets, enteric-coated tablets, syrups, emulsions, suspensions, or as solid forms suitable for solution or suspension in liquid prior to administration. Suitable excipients are, for example, water, saline, dextrose, mannitol, lactose, lecithin, albumin, sodium glutamate, cysteine hydrochloride or the like. In addition, if desired, the pharmaceutical compositions may contain minor amounts of nontoxic auxiliary substances, such as wetting agents, pH buffering agents, and the like. If desired, absorption enhancing preparations (e.g., liposomes) may be utilized.

In selected cases, drug delivery vehicles may be employed for systemic or topical administration. They can be designed to serve as a slow release reservoir, or to deliver their contents directly to the target cell. An advantage of using direct delivery drug vehicles is that multiple molecules are delivered per vehicle uptake event. Such vehicles have been shown to also increase the circulation half-life of drugs which would otherwise be rapidly cleared from the blood stream. Some examples of such specialized drug delivery vehicles which fall into this category are liposomes, hydrogels, cyclodextrins, biodegradable polymers (surgical implants or nanocapsules), and bioadhesive microspheres.

For example, a liposome delivery vehicle originally designed as a research tool, Lipofectin, has been shown to deliver intact molecules to cells. Liposomes offer several advantages: They are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for an agent. These carriers have been developed for chemotherapeutic agents.

Topical administration of agents is advantageous since it allows localized concentration at the site of administration with minimal systemic adsorption. This simplifies the delivery strategy of the agent to the disease site and reduces the extent of toxicological characterization. Furthermore, the amount of material to be administered is far less than that required for other administration routes.

Effective delivery may require the agent to diffuse into the target cells. Chemical modification of the agent may be all that is required for penetration. However, in the event that such modification is insufficient, the modified agent can be co-formulated with permeability enhancers, such as Azone or oleic acid, in a liposome. The liposomes can either represent a slow release presentation vehicle in which the modified agent and permeability enhancer transfer from the liposome into the target cell, or the liposome phospholipids can participate directly with the modified agent and permeability enhancer in facilitating cellular delivery.

Agents may also be systemically administered. Systemic absorption refers to the accumulation of drugs in the blood stream followed by distribution throughout the entire body. Administration routes which lead to systemic absorption include: oral, intravenous, subcutaneous, intraperitoneal, intranasal, intrathecal and ocular. Each of these administration routes exposes the agent to an accessible target tissue. Subcutaneous administration drains into a localized lymph node which proceeds through the lymphatic network into the circulation. The rate of entry into the circulation has been shown to be a function of molecular weight or size. The use of a liposome or other drug carrier can localize the agent at the lymph node and participate in the delivery of the agent to the cell.

Intraperitoneal administration also leads to entry into the circulation with the molecular weight or size of the agent-delivery vehicle complex controlling the rate of entry.

Liposomes injected intravenously show accumulation in the liver, lung and spleen. The composition and size can be adjusted so that this accumulation represents 30% to 40% of the injected dose. The rest is left to circulate in the blood stream for up to 24 hours.

The examples provided herein are provided solely for the purpose of illustration and are in no way meant to limit the scope of this invention.

EXAMPLES

Example 1
Cloning of cDNAs for 4E-BP1 and 4E-BP2

The "interaction cloning" technique was used to identify proteins which interact with eIF-4E. A cDNA clone encoding eIF-4E was modified at the terminus by inserting the phosphorylation site for the heart muscle kinase (HMK) (Blanar & Rutter, *Science* 256, 1014–1018, 1992). The recombinant protein was expressed in *E. coli* and purified on a m$^7$GDP-affinity column to homogeneity (Edery et al., *Gene* 74, 517–525, 1988). It was labelled using [$\gamma$-$^{32}$P]ATP and bovine heart muscle kinase (Sigma) to a specific activity of $1\times10^8$ cpm/$\mu$g, and used to screen a human placenta $\lambda$gt 11 cDNA library in a "far-Western assay" (Blanar & Rutter, 1992). Approximately 1 million plaques were screened and nine plaques which interacted with the eIF-4E probe were isolated. The cDNA inserts of positive $\lambda$ plaques were released with Sal I, subcloned into pBluescript KS (Stratagene), and sequenced completely in both orientations. Three of the positive plaques contained clones corresponding to the p220 subunit of the cap-binding complex (eIF-4F), as would be expected. The other positive isolates contained two distinct, but related sequences that were named 4E-BP1 and 4E-BP2 (for 4E-binding protein 1 and 2). Two phage isolates contained the 4E-BP1 sequence and one isolation of 4E-BP2 was made. The cDNAs for 4E-BP1 and 4E-BP2 encode proteins of 118 and 120 amino acids, respectively (see figures). Northern blot analysis demonstrated, however, that the mRNAs encoding the two proteins are quite different in size: the mRNA encoding 4E-BP1 is about 850 nucleotides long, while that of 4E-BP2 is about 2800 nucleotides in length. The sequences of the two proteins are shown in the figures. The two protein sequences are 56% identical.

Example 2
Homology between 4E-BP1 and PHAS-I

By searching a DNA database, a high degree of identity (93%, and 97% similarity) was found between the protein sequence of the human 4E-BP1, and a recently published cDNA encoding a rat protein termed PHAS-I (Hu et al. *Proc. Natl. Acad. Sci. USA* 91, 3730–3734 (1994); FIG. 2). This indicates that the 4E-BP1 is the human homologue of PHAS-I, which was initially identified as a protein phosphorylated in response to insulin in rat adipose tissue and in murine 3T3-L1 adipocytes.

Example 3
Fusion Proteins

Plasmids expressing 4E-BP1 and 4E-BP2 in the form of readily purified fusion proteins were constructed as follows. 4E-BP1 cDNA was released from pBluescript KS by digestion with Pvu II and Eco RI (this results in the deletion of three N-terminal amino-acids), and subcloned into pGEX-2T cleaved with Sma I and Eco RI, to generate plasmid pGEX-2T-4E-BP1. 4E-BP2 cDNA was released from $\lambda$gt 11 DNA by digestion with EcoR I and subcloned into Eco RI-digested plasmid pGEX-2T[128/129], to generate pGEX-2T[128/129]-4E-BP2. pGEX-2T[128/129], and thus pGEX-2T[128/129]-4E-BP2, contain an HMK flag. Glutathione S-transferase (GST and the fusion proteins GST-4E-BP1 and GST-4E-BP2 were expressed in *E.coli* BL21 from, respectively, pGEX-2T, pGEX-2T-4E-BP1, and pGEX-2T[128/129]-4E-BP2, and purified as described (Methot et al., *Mol. Cell. Biol.* 14, 2307–2316, 1994). Histidine-tagged PHAS-I protein (His-Tag-PHAS-I) was expressed in *E.coli* BL21 (DE3), and purified on a HisBind resin (Novagen).

Example 4
Interaction of 4E-BP1 and 4E-BP2 with eIF-4E

To confirm that 4E-BP1 and 4E-BP2, as well as rat PHAS-I, interact with eIF-4E, the recombinant fusion proteins GST-4E-BP1, GST-4E-BP2 and His-Tag-PHAS-I were analyzed for interaction with eIF-4E by the "far Western" technique. Purified samples of GST (400 ng), GST-4E-BP1 (600 ng), GST-4E-BP2 (600 ng), and His-Tag-PHAS-I (200ng) were separated on a SDS 15%-polyacrylamide gel, transferred to nitrocellulose membrane, and incubated with $^{32}$P-labelled HMK-eIF-4E probe ($2.5\times10^5$ cpm/ml). The membrane was washed and exposed against an X-ray film to detect bound probe. While no discrete band of bound HMK-eIF-4E was observed in the lane containing GST alone, such bands were clearly visible in the lanes containing GST-4E-BP1, GST-4E-BP2 and PHAS-I. HMK-eIF-4E interacted with comparable strength with both GST-4E-BP1 and GST-4E-BP2. PHAS-I migrated as a 22 kD protein on SDS-PAGE, but the calculated size of the protein from its sequence is only about 12 kD. This characteristic is also shared with 4E-BPs that were synthesized using in vitro translation systems.

Example 5
Immunoprecipitation

The interaction of 4E-BP1 with eIF-4E was confirmed by co-immunoprecipitation experiments using 4E-BP1 and eIF-4E synthesized by in vitro translation in wheat germ extract, which was used rather than rabbit retioulocyte lysate because the latter was found to contain endogenous 4E-BP1. These experiments were performed for 4E-BP1 [PHAS-I] only, because an antibody against 4E-BP2 is not presently available.

Plasmids pKS-eIF-4E and pKS4E-BP1 were linearized with Sal I and BamH I respectively, and transcribed with T7 and T3 RNA polymerase respectively in the presence of m$^7$GpppG to yield capped transcripts as described (Pelletier & Sonenberg, *Cell* 40, 515–526, 1985). mRNAs (10 $\mu$g/ml) encoding eIF-4E or 4E-BP1 were translated separately or together using wheat-germ extract (Promega) with [$^{35}$S]-methionine for 1 h at 25° C. Reaction 1 contained eIF-4E mRNA alone, reaction 2 contained 4E-BP1 mRNA alone, and reaction 3 contained both mRNAs. Following translation, samples were analyzed directly or incubated with rabbit anti-PHAS-I (4E-BP1) antiserum (2 $\mu$l) and 300 $\mu$l of 3% protein A-sepharose (Pharmacia) suspension in TBS (20 mM Tris.HCl, pH 7.4, 0.9% NaCl) for 1 h at 40° C. The resin was washed (3×1 ml) with 50 mM Tris-HCl, pH 7.5, 150 mM KCl, 1% NP40, 1 mM EDTA, and eluted proteins were separated on a SDS 15%-polyacrylamide gel, which was then fixed, treated with EN³Hance (DuPont), and exposed to X-ray film. The lanes in which the translation products of reaction 1 were analyzed directly showed a band at the position expected for eIF-4E; no bands were visible in the lane containing the sample obtained by applying the immunoprecipitation procedure with anti-PHAS-I (4E-BP1) antiserum to the translation products of reaction 1. The lanes corresponding to reaction 2 showed a protein, presumably 4E-BP1, with an apparent molecular weight of about 20 kD which was present in the translation reaction products analyzed directly and also in the products precipitated with anti-PHAS-I (4E-BP1) antiserum. The lanes corresponding to reaction 3 showed two proteins, presumably eIF-4E and 4E-BP1, both of which were present in the translation reaction products analyzed directly and the products precipitated with anti-PHAS-I (4E-BP1) antiserum. These results indicate that anti-PHAS-I antiserum was specific for 4E-BP1 and did not recognize eIF-4E directly, and that eIF-4E and 4E-BP1 form a complex which is also recognized by the antiserum. Similar results were obtained using anti-eIF-4E antiserum, and neither protein was immunoprecipitated by pre-immune serum.

Example 6
Use of m⁷GDP-affinity Resin to Study Binding of 4E-BP1 to eIF-4E mRNAs (4g/ml) encoding eIF-4E and 4E-BP1 were translated in wheat germ extract separately or together as described in Example 5. Translation products were incubated with m⁷GDP-affinity resin in buffer A (20 mM Tris-HCl, pH 7.5, 100 mM KCl, 2mM DTT, 2mM EDTA), the resin was washed (3×1 ml) in buffer A, and bound proteins were eluted in SDS sample buffer and analyzed as described in Example 5. The results indicated that eIF-4E synthesized in reaction 1 recognized the cap structure and bound to the resin, as expected. 4E-BP1 synthesized by itself in reaction 2 failed to bind to the resin, but 4E-BP1 synthesized with concomitant synthesis of eIF-4E in reaction 3 was retained by the resin. This demonstrates that the interaction of 4E-BP1 with eIF-4E does not preclude the binding of eIF-4E to the cap-structure.

Example 7
Analysis of 4E-BP1 in Insulin-treated Tissue

Epididymal fat pads from six male Sprague-Dawley rats (about 150 g) were incubated pairwise, in three separate pools, in Dulbecco's Modified Eagle's Medium for 30 min, and for a further 30 min in fresh media in the absence or presence of 80 nM insulin. The tissue was frozen rapidly in liquid nitrogen and extracted in cold buffer containing 0.25M sucrose, 10 mM Tris-HCl, pH7.5, 5 mM EDTA, 2 mM EGTA, using a Brinknan PT-10 polytron. The homogenate was centrifuged at 8,000 rpm for 5 min, and the infranatant was collected. Aliquots were treated at 100° C. for 7 min, and the precipitated proteins were removed by centrifugation. This heat treatment enriches for the heat stable 4E-BP1 protein. Soluble proteins remaining after the heat treatment were precipitated with trichloroacetic acid (15%). Samples were analysed by SDS-PAGE and transferred to a nitrocellulose membrane. The membrane was processed for far-Western analysis as described in Example 4. The binding of the ³²P-labelled HMK-eIF-4E was quantified using a Phosphorimager device. The results were as follows:

| Tissue pool | Pool 1 | | Pool 2 | | Pool 3 | |
|---|---|---|---|---|---|---|
| Insulin treatment | − | + | − | + | − | + |
| Relative amount of HMK-eIF-4E bound | 152 | 41 | 210 | 70 | 214 | 60 |
| Fold reduction | | 3.7 | | 3.0 | | 3.6 |

Thus 4E-BP1 prepared from insulin-treated tissue bound HMK-eIF-4E to a significantly lower extent than 4E-BP1 prepared from untreated tissue. Analysis of the cell extracts using an antiserum raised against the carboxy-terminus of PHAS-I/4E-BP1 demonstrated that the treatment with insulin had no significant effect on the total amount of 4E-BP1. These results demonstrate that the interaction between eIF-4E and 4E-BP1 is decreased in response to insulin.

To examine the role played by phosphorylation in the reduced affinity of 4E-BP1 in insulin-treated tissue for eIF-4E, portions of each homogenate were treated with potato acid phosphatase (PAPase) prior to analysis by the far-Western technique. The PAPase treatment was inserted after the removal by centrifugation of proteins precipitated during the heat treatment at 100° C. Samples were incubated with 6 units of potato acid phosphatase (PAPase) in 100 mM MES (Sigma), pH 6.0 for 30 minutes at 37° C., then reheated to 100° C. and processed further as described above. The results clearly demonstrated that when the samples were treated with phosphatase, the binding of eIF-4E to 4E-BP1 in insulin-treated extracts was augmented, and was similar to that in control extracts. Thus the reduced ability of 4E-BP1 in insulin-treated cells to bind eIF-4E is due to phosphorylation of 4E-BP1.

Example 8
Analysis of Effect of Insulin on Association Between eIF-4E and 4E-BP1 in vivo The interaction between 4E-BP1 with eIF-4E in vivo was studied further by determining whether a m⁷GDP-affinity column could capture 4E-BP1 from extracts prepared from insulin-treated and untreated adipose tissue. Capture of 4E-BP1 requires that interact with eIF-4E, because it is the latter which actually binds to the m⁷GDP ligand on the affinity column. Rat adipose tissue was incubated as described in Example 7 in the absence or presence of insulin (80 nM) for 30 minutes. The tissue was then frozen rapidly in liquid nitrogen and extracted in cold buffer containing 0.25M sucrose, 10 mM Tris-HCl, pH7.5, 5 mM EDTA, 2 mM EGTA, using a Brinkman PT-10 polytron. The homogenate was centrifuged at 8,000 rpm for 5 min, and the infranatant was collected. The infranatant was incubated with m⁷GDP-coupled agarose washed (3×1 ml) with buffer A (20 mM Tris-HCl, pH 7.5, 100 mM KCl, 2 mM DTT, 2 mM EDTA). A parallel incubation was performed using agarose which had not been coupled with m⁷GDP. Proteins bound to the resins were eluted with SDS-sample buffer and analyzed in Western blots utilizing antibodies specific for 4E-BP1 (PHAS-I) and eIF-4E, as follows. The proteins were separated by SDS-PAGE and transferred to a nitrocellulose membrane, which was incubated in TBS/5% milk/0.1% Tween 20 and then simultaneously with rabbit anti-eIF-4E (1:2000) and rabbit anti-PHAS-I(4E-BP1) antibody (2 g/ml). Horseradish peroxidase-conjugated anti-rabbit IgG was then added to the incubation, and bound antibody detected using an ECL kit (Amersham). Lanes 1–4 on the gel corresponded to extracts prepared from one pool of adipose tissue from two animals, lanes 5 and 6 to extracts from a second pool. Lanes 1 and 2 correspond to samples incubated with agarose that had not been coupled to m⁷GDP, lanes 3–6 to samples incubated with m⁷GDP-coupled agarose. No bands were visible in lanes 1 or 2, indicating that neither eIF-4E nor 4E-BP1 (PHAS-I) bound to the uncoupled resin. Bands corresponding to eIF-4E, and of about equal intensity, were observed in each of lanes 3–6, indicating that treatment with insulin had little effect on the amount of eIF-4E in an extract which could bind to m⁷GDP-coupled agarose. The bands corresponding to 4E-BP1 were of significantly reduced intensity in lanes 4 and 6, which contained samples derived from insulin-treated tissue, compared with lanes 3 and 5, which contained samples derived from untreated tissue. Thus insulin treatment significantly reduces the amount of 4E-BP1 capable of binding to m⁷GDP-coupled agarose via eIF-4E, indicating that insulin significantly decreases the association between 4E-BP1 and eIF-4E.

Example 9

Analysis of insulin-induced Phosphorylation of 4E-BP1 and Dissociation from eIF-4E 3T3-L1 cells, which express insulin receptors, were incubated with inorganic [$^{32}$P]-phosphate in the presence or absence of insulin. $^{32}$P-labelled 4E-BP1 and eIF-4E were immunoprecipitated using PHAS-I (4E-BP1) antiserum as described in example 5. Insulin treatment enhanced the phosphorylation of 4E-BP1, and reduced the amount of eIF-4E which co-precipitated with 4E-BP1. Thus phosphorylation of 4E-BP1 in response to insulin exposure results in dissociation of 4E-BP1 from eIF-4E, suggesting that this may account for the enhanced translation activity observed in adipose tissue upon insulin treatment.

Example 10

In vitro Translation of Bicistronic RNAs

To investigate the possibility that interaction of the 4E-BPs with eIF-4E interferes with cap-dependent translation, but not cap-independent translation, translations were performed using artificial bicistronic mRNA containing the EMCV IRES (Edery et al., 1988). Translation of chloramphenicol acetyl transferase (CAT) from this RNA is cap- and eIF-4E-dependent, but translation of luciferase (LUC) directed by the EMCV IRES is cap-independent. Capped bicistronic RNA was produced from Xho I-linearized pGEMCAT/EMC/LUC using T7 RNA polymerase. Standard aliquots of rabbit reticulocyte lysate were preincubated for 10 minutes with either purified GST (400 ng), purified GST4E-BP1 (600ng), or purified GST-4E-BP2 (600 ng). Recombinant eIF-4E (400ng) was also added in some cases, either at the beginning of the pre-incubation or at the end. Each aliquot of lysate was then used for in vitro translation of capped bicistronic RNA, initiated by the addition of this RNA (to a final concentration of 7 µg/ml) and amino acids (including [$^{35}$S]-methionine), and continued for 30-minutes at 30° C. Translation products were then separated by SDS-PAGE, and radioactivity incorporated into CAT and LUC was quantified using a Phosphorimager. The amount of CAT and LUC synthesized in each reaction was determined in arbitrary units by expressing the radioactivity detected in CAT and in LUC in each reaction as a percentage of the radioactivity detected in CAT and in LUC, respectively, in the reaction performed using lysate precincubated with GST alone. Results were as follows:

|  | Reaction | | | | | | | |
| --- | --- | --- | --- | --- | --- | --- | --- | --- |
|  | 1 | 2 | 3 | 4 | 5 | 6 | 7 | 8 |
| Preincubated with: | | | | | | | | |
| GST for 10' | X | X | | | | | | |
| GST-4E-BP1 for 10' | | | X | | X | | X | |
| GST-4E-BP2 for 10' | | | | X | | X | | X |
| eIF-4E for 10' | | X | | | X | X | | |
| eIF-4E for 0' | | | | | | | X | X |
| CAT (%) | 100 | 139 | 18 | 20 | 137 | 138 | 130 | 115 |
| LUC (%) | 100 | 115 | 74 | 73 | 116 | 119 | 106 | 96 |

Thus translation of bicistronic RNA in rabbit reticulocyte lysate produced both CAT and LUC efficiently. Preincubation of the lysate for 10 minutes, prior to the addition of RNA, with purified GST-4E-BP1 or GST-4E-BP2 specifically inhibited translation of CAT (which is cap-dependent) by about 5-fold (reactions 3 and 4, respectively). Little effect was seen on translation of luciferase (which is cap-independent) under these conditions. The inhibitory effects of GST-4E-BP1 or GST-4E-BP2 on cap-dependent translation of CAT could be relieved by addition of recombinant eIF-4E regardless of whether it was present during the pre-incubation of the 4E-BPs with the reticulocyte lysate (reactions 5 and 6), or added after the pre-incubation period (reactions 7 and 8). This suggests that the formation of the 4E-BP-eIF-4E complex does not irreversibly inhibit the translational machinery.

Example 11

Translation of Bicistronic RNAs in vivo

To investigate whether the 4E-BPs inhibit cap-dependent translation in vivo, the same bicistronic reporter system was analyzed using a transient expression assay within cells infected with the recombinant vaccinia virus vTF7-3, which expresses the T7 RNA polymerase (Fuerst et a., Proc. Natn. Acad. Sci. USA 83, 8122–8126, 1986; Belsham & Brangwyn, J. Virol. 64, 5389–5395, 1990). Human HTK-143 cells (ATCC) were infected with virus vTF7-3 and transfected with 2 µg of a "reporter" plasmid encoding a bicistronic RNA, either pGEMCAT/polio/LUC or pGEMCAT/EMC/LUC, pGEMCAT/EMC/LUC is described in Example 10. pGEMCAT/polio/LUC is a similar plasmid whose transcripts contain the poliovirus IRES instead of the EMCV IRES, and direct translation of LUC in a cap-independent manner. Transfections were performed using 15 µg of lipofectin (BRL). In some cases 5 µg of an additional plasmid was co-transfected with the reporter plasmid, this additional plasmid being derived from pRc/CMV (Invitrogen) and containing the coding sequence of either 4E-BP1 or 4E-BP2 under control of the T7 promoter. After 20 hours cell extracts were prepared, and CAT and LUC expression were measured by, respectively, an ELISA assay (Boehringer Mannheim) and an enzyme assay using a luciferase assay system (Promega) and a luminometer (BIOORBIT). For each reporter protein, results for a given series of transfections were expressed as a percentage of the amount of that protein measured in cells transfected by the reporter plasmid alone. The results were:

| | Transfection | | | | | |
|---|---|---|---|---|---|---|
| | 1 | 2 | 3 | 4 | 5 | 6 |
| pGEMCAT/EMC/LUC | X | X | X | | | |
| pGEMCAT/polio/LUC | | | | X | X | X |
| pRc/CMV/4E-BP1 | | X | | | X | |
| pRc/CMV/4E-BP2 | | | X | | | X |
| CAT (%) | 100 | 28 | 26 | 100 | 22 | 24 |
| LUC (%) | 100 | 115 | 102 | 100 | 108 | 117 |

Thus efficient expression of CAT and LUC was observed from pGEMCAT/polio/LUC or pGEMCAT/EMC/LUC mRNAs, when transfected alone. When plasmids encoding 4E-BP1 or 4E-BP2 were co-transfected with either of the reporter plasmids, specific inhibition (4–5 fold) of CAT expression was observed, with little effect on luciferase expression, Hence, 4E-BP1 and 4E-BP2 are specific inhibitors of cap-dependent translation in vivo as well as in vitro.

Example 12
Screening of compounds a) Plasmid construction

Plasmid pSS/LUC (for secondary structure/luciferase) is constructed by inserting several copies of a palindromic DNA sequence (a Xho I linker) in the region of a luciferase plasmid (pGEM-luc) from which the luciferase 5'-UTR is transcribed. pGEM-luc (Promega) DNA is digested with Not I and the ends filled in using the Klenow fragment of *E. coli* DNA polymerase I. 8-mer Xho I linkers (Promega) were phosphorylated using T4 polynucleotide kinase and ligated using T4 DNA ligase to form multimers which were then ligated using the same enzyme into the filled-in Not I site in pGEM-luc. Plasmids were amplified in *E. coli* strain HB101 and colonies analyzed for their susceptibility to Xho I digestion. Plasmids with Xho I linker(s) inserted at the Not I site yield two fragments on digestion with Xho I; plasmids lacking Xho I linkers are merely linearized at the Xho I site downstream of the luc coding sequence. Plasmids containing Xho I linkers were sequenced using the pUC/M13 reverse sequencing primer, and a plasmid was selected which contained five copies of the Xho I linker. This plasmid was designated pSS/LUC.

b) Transcription of capped RNA Capped SS/LUC RNA is synthesized by transcribing Sal I-linearized pSS/LUC DNA using the mMESSAGE mMACHINE SP6 Kit from Ambion (Austin, Tex.) in accordance with the manufacturer's instructions. The RNA is precipitated with ethanol and redissolved in TE buffer (10 mM Tris.HCl, pH 8.0, 1 mM EDTA) at a concentration of 100 µg/ml.

Capped bicistronic CAT/EMC/LUC RNA containing the luciferase coding sequence downstream of the EMCV IRES is produced from Xho I-linearized pGEMCAT/EMC/LUC using the mMESSAGE mMACHINE T7 Kit from Ambion. The RNA Is precipitated with ethanol and redissolved in TE buffer (10 mM Tris.HCl, pH 8.0, 1 mM EDTA) at a concentration of 100 µg/ml.

c) Translation of capped RNA

Capped SS/LUC RNA is translated in rabbit reticulocyte lysate (Promega) in accordance with the manufacturers instructions. The reactions are performed in the wells of 96-well microtiter plates. The amount of luciferase synthesized in each well is quantified using an Enhanced Luciferase Assay Kit (Analytical Luminescence, Inc). Several translations are performed containing different amounts of SS/LUC RNA, and the smallest amount of SS/LUC RNA which gives maximal synthesis of luciferase is selected for use in compound screening.

d) Luciferase assays

Luciferase activity is measured using reagents provided in an Enhanced Luciferase Assay Kit (Analytical Luminescence, Inc). 50 µl of "buffer A" and 50 µl of "buffer B" are added to each well, and light output in relative light units (RLU) is measured using a Dynatech 3000ML luminometer in cycle mode.

e) Translation of capped RNA in presence of test compounds

4 µl of a stock of SS/LUC RNA, containing the amount of RNA determined in the previous step to be optimal, is added to each well of a 96-well microtiter plate. Solutions of 80 different test compounds dissolved in 3.33% DMSO are added separately to 80 of the wells, with 4 µL of each solution added to each well. 16 wells each receive 4 µl of 3.33% DMSO instead of a solution of a test compound; these wells serve as controls. A translation cocktail consisting of 800 µ of rabbit reticulocyte lysate and 60 µl of an amino acid solution containing each of the 20 amino acids at a concentration of 1 mM was prepared, and 7.5 µl of this cocktail was added to each well. The plate is then incubated at 30° C. for 60 minutes, and the luciferase activity in each well is measured.

f) Retesting of compounds using bicistronic RNA

The luciferase activity measured in translations of SS/LUC RNA that contained test compounds is compared with that measured in wells that contained control reactions. Compounds which cause an increase or decrease in measurable luciferase activity may be doing so by affecting eIF-4E-mediated initiation of translation. Such compounds are then tested in parallel in vitro translation reactions using both the SS/LUC RNA and CAT/EMC/LUC RNA. Compounds which cause an increase or decrease in luciferase activity translated from SS/LUC RNA but do not have the same impact on luciferase activity translated from CAT/EMC/LUC RNA are very likely to be affecting eIF-4E-mediated initiation of translation, and are selected for further study as potential agents for the treatment of hormone disorders.

Other embodiments are within the following claims.

What is claimed is:

1. A purified human nucleic acid sequence encoding a cellular component that binds to eIF-4E and causes a modulation of translation in a cell in response to a hormone comprising a coding sequence for the protein 4E-BP 1.

2. A purified human nucleic acid sequence encoding a cellular component that binds to eIF-4E and causes a modulation of translation in a cell in response to a hormone comprising a coding sequence for the protein 4E-BP2.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:

(A) LENGTH: 357 base pairs
        (B) TYPE: nucleic acid
        (C) STRANDEDNESS: single
        (D) TOPOLOGY: linear (xi) SEQUENCE DESCRIPTION: SEQ ID NO: 1:

ATG TCC GGG GGC AGC AGC TGC AGC CAG ACC C CA AGC CGG GCC ATC CCC         48
Met Ser Gly Gly Ser Ser Cys Ser Gln Thr P ro Ser Arg Ala Ile Pro
 1               5                  10                  15

GCC ACT CGC CGG GTG GTG CTC GGC GAC GGC G TG CAG CTC CCG CCC GGG         96
Ala Thr Arg Arg Val Val Leu Gly Asp Gly V al Gln Leu Pro Pro Gly
                20                  25                  30

GAC TAC AGC ACG ACC CCC GGC GGC ACG CTC T TC AGC ACC ACC CCG GGA        144
Asp Tyr Ser Thr Thr Pro Gly Gly Thr Leu P he Ser Thr Thr Pro Gly
            35                  40                  45

GGT ACC AGG ATC ATC TAT GAC CGG AAA TTC C TG ATG GAG TGT CGG AAC        192
Gly Thr Arg Ile Ile Tyr Asp Arg Lys Phe L eu Met Glu Cys Arg Asn
50                  55                  60

TCA CCT GTG ACC AAA ACA CCC CCA AGG GAT C TG CCC ACC ATT CCG GGG        240
Ser Pro Val Thr Lys Thr Pro Pro Arg Asp L eu Pro Thr Ile Pro Gly
65                  70                  75                  80

GTC ACC AGC CCT TCC AGT GAT GAG CCC CCC A TG GAA GCC AGC CAG AGC        288
Val Thr Ser Pro Ser Ser Asp Glu Pro Pro M et Glu Ala Ser Gln Ser
                85                  90                  95

CAC CTG CGC AAT AGC CCA GAA GAT AAG CGG G CG GGC GGT GAA GAG TCA        336
His Leu Arg Asn Ser Pro Glu Asp Lys Arg A la Gly Gly Glu Glu Ser
            100                 105                 110

CAG TTT GAG ATG GAC ATT TAA                                             357
Gln Phe Glu Met Asp Ile *
        115

(2) INFORMATION FOR SEQ ID NO: 2:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (xi) SEQUENCE DESCRIPTION: SEQ ID NO: 2:

ATG TCC TCG TCA GCC GGC AGC GGC CAC CAG C CC AGC CAG AGC CGC GCC         48
Met Ser Ser Ser Ala Gly Ser Gly His Gln P ro Ser Gln Ser Arg Ala
 1               5                  10                  15

ATC CCC ACC CGC ACC GTG GCC ATC AGC GAC G CC GCG CAG CTA CCT CAT         96
Ile Pro Thr Arg Thr Val Ala Ile Ser Asp A la Ala Gln Leu Pro His
                20                  25                  30

GAC TAT TGC ACC ACG CCC GGG GGG ACG CTC T TC TCC ACC ACA CCG GGA        144
Asp Tyr Cys Thr Thr Pro Gly Gly Thr Leu P he Ser Thr Thr Pro Gly
            35                  40                  45

GGA ACT CGA ATC ATT TAT GAC AGA AAG TTT C TG TTG GAT CGT CGC AAT        192
Gly Thr Arg Ile Ile Tyr Asp Arg Lys Phe L eu Leu Asp Arg Arg Asn
50                  55                  60

TCT CCC ATG GCT CAG ACC CCA CCC TGC CAT C TG CCC AAT ATC CCA GGA        240
Ser Pro Met Ala Gln Thr Pro Pro Cys His L eu Pro Asn Ile Pro Gly
65                  70                  75                  80

GTC ACT AGC CCT GGC ACC TTA ATT GAA GAC T CC AAA GTA GAA GTA AAC        288
Val Thr Ser Pro Gly Thr Leu Ile Glu Asp S er Lys Val Glu Val Asn
                85                  90                  95

AAT TTG AAC AAC TTG AAC AAT CAC GAC AGG A AA CAT GCA GTT GGG GAT        336
Asn Leu Asn Asn Leu Asn Asn His Asp Arg L ys His Ala Val Gly Asp
            100                 105                 110

GAT GCT CAG TTC GAG ATG GAC ATC TGA                                     363

Asp Ala Gln Phe Glu Met Asp Ile *
    115                 120

(2) INFORMATION FOR SEQ ID NO: 3:

(i) SEQUENCE CHARACTERISTICS:
        (A) LENGTH: 829 base pairs
        (B) TYPE: nucleic acid
        (C) STRANDEDNESS: single
        (D) TOPOLOGY: linear (xi) SEQUENCE DESCRIPTION: SEQ ID NO: 3:

```
GTTCGCGGGT GCAGCGCACA GGAGATCATG TCCGGGGGCA GCAGCTGCAG             50

CCAGACCCCA AGCCGGGCCA TCCCCGCCAC TCGCCGGGTG GTGCTCGGCG            100

ACGGCGTGCA GCTCCCGCCC GGGGACTACA GCACGACCCC CGGCGGCACG            150

CTCTTCAGCA CCACCCCGGG AGGTACCAGG ATCATCTATG ACCGGAAATT            200

CCTGATGGAG TGTCGGAACT CACCTGTGAC CAAAACACCC CCAAGGGATC            250

TGCCCACCAT TCCGGGGGTC ACCAGCCCTT CCAGTGATGA GCCCCCCATG            300

GAAGCCAGCC AGAGCCACCT GCGCAATAGC CCAGAAGATA AGCGGGCGGG            350

CGGTGAAGAG TCACAGTTTG AGATGGACAT TTAAAGCACC AGCCATCGTG            400

TGGAGCACTA CCAAGGGGCC CCTCAGGGCC TTCCTGGGAG GAGTCCCACC            450

AGCCAGGCCT TATGAAAGTG ATCATACTGG GCAGGCGTTG GCGTGGGGTC            500

GGACACCCCA GCCCTTTCTC CCTCACTCAG GGCACCTGCC CCCTCCTCTT            550

CGTGAACACC AGCAGATACC TCCTTGTGCC TCCACTGATG CAGGAGCTGC            600

CACCAAGGGG AGTGACCCCT GCCAGCACAC CCTGCAGCCA AGGGCAGGA             650

AGTGGACAAG AACGAACCCT TCCTTCCGAA TGATCAGCAG TTCCAGCCCC            700

TCGCTGCTGG GGGCGCAACC ACCCCTTCCT TAGGTTGATG TGCTTGGGAA            750

AGCTCCCTCC CCCTCCTTCC CCAAGAGAGG AAATAAAAGC CACCTTCGCC            800

CTAGGGCCAA GAAAAAAAAA AAAAAAAA                                   829
```

(2) INFORMATION FOR SEQ ID NO: 4:

(i) SEQUENCE CHARACTERISTICS:
        (A) LENGTH: 1673 base pairs
        (B) TYPE: nucleic acid
        (C) STRANDEDNESS: single
        (D) TOPOLOGY: linear (xi) SEQUENCE DESCRIPTION: SEQ ID NO: 4:

```
CGGAAGCCCG CGCCCACAGC CATGTCCTCG TCAGCCGGCA GCGGCCACCA             50

GCCCAGCCAG AGCCGCGCCA TCCCCACCCG CACCGTGGCC ATCAGCGACG            100

CCGCGCAGCT ACCTCATGAC TATTGCACCA CGCCCGGGGG GACGCTCTTC            150

TCCACCACAC CGGGAGGAAC TCGAATCATT TATGACAGAA AGTTTCTGTT            200

GGATCGTCGC AATTCTCCCA TGGCTCAGAC CCCACCCTGC CATCTGCCCA            250

ATATCCCAGG AGTCACTAGC CCTGGCACCT TAATTGAAGA CTCCAAAGTA            300

GAAGTAAACA ATTTGAACAA CTTGAACAAT CACGACAGGA AACATGCAGT            350

TGGGGATGAT GCTCAGTTCG AGATGGACAT CTGACTCTCC TGCAAGGATT            400

AGAAGAAAAG CAGCAACACT GATACTTGTG TGCACCTGAT TTGGCCAATA            450

GGATCAACAG TGAAAAGACA GAAGAGGCAA TACCAGCAGT CCCCATTACA            500
```

```
GTCTCCACCT CCCCGTCTTC CTCTGGGTGC CAAATGATGG GAAGATGAGC        550

TTCATCTGAC CATTTCTTCT CCCTGTCTCC TGTTCCCCTT CCCAGTTCCC        600

AGTTAAACAG GTTAGATTGA AGGCCCTTGC TGTATTTCTG TAGAGCTAAG        650

CAGCCCTTAG AGGAAAACAG TTCAACTCTG ACTTTCCTAG TTGTTTTTTT        700

ATTGAGAGCC ACCCTCATAC CCTGTAATTT TGTCCCAAAT CAAATATCAA        750

CCTACCAACA ACTGCCTGGC TGGGAAGTCT GGGGAAGGGA TACAGAGCTT        800

GGTGGGCCTA ACACCATTCA TATTCCTTAC CCTCTGTCTC TCCTCCCTGT        850

ATCCCACCTA TGGTTCAGTG TTGCAAGAGT CTGGGCTTGG GGTCTTTAAA        900

ACCAGCAGGG GGAAATGATA AAAAGAGAGC TGCTTTCCCT TTTACCTTGA        950

GGTATTCGTC CCTCGGGACA GAGCACAGCT TGTGCAACTC TGGTAGCGTT       1000

ACCCTTGTGC AACTCTGGTA GCGTTACCCT GTGACACTGT TTTGAGGTCC       1050

ACTTCCTTTC TTTCCTCTGG GAGGAATGTC TTCTGTCTTT GGTATTATAG       1100

TTCATCTTCC CATTCTTTTA CTTAGTGCAT TTGTGCAGAT ATTTTTAACT       1150

CTGTACATCA GAAGAGAGCC CTTGGTAACC AGTTTTGCTC TTCTTCTGCC       1200

ACTCCTCCCT GCTTGCATCT CGTTGCTGGC AGAGTCCTCT TGTACTTCAA       1250

GAAAGCAAAG TGATTTTGTC TGCCTCCTAG AGCAGGTCCA TACCAAGTAA       1300

TAGAGGCACT TTAGCTTCCA CTTGGTGGGT AAGGCCTGAT CATAGTATTC       1350

TGTCAGATAA TGCCTAAGAA TGACCGCTGG GGGTGGAGCT CCATCATCAA       1400

ATGGCCAATC TAGAACGTGG ATTCCTTCTT TTTCAACTGG AGCTTTATCA       1450

TATGTAGCAT CACAAACTCG AACCAAAGTC GTCACTCCAT ACTTCGGTAG       1500

CAGTCGACAG ATGAATTCCA GCTGAGCGCC GGTCGCTACC ATTACCAGTT       1550

GGTCTGGTGG GGGATCCACT AGTTCTAGAG CGGCCGCCAC CGCGTGGAGC       1600

TAATTCGCCC TATAGTGAGT CGTATTACAA TTCACTGGCC GTCGTTTTAC       1650

AACGTCGTGA CTGGGAAACC TGG                                    1673
```